(12) United States Patent
Rao et al.

(10) Patent No.: US 8,152,844 B2
(45) Date of Patent: Apr. 10, 2012

(54) QUICK-RELEASE ANNULOPLASTY RING HOLDER

(75) Inventors: Anand R. Rao, Irvine, CA (US); Hilda Z. Fann, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 243 days.

(21) Appl. No.: 12/437,474

(22) Filed: May 7, 2009

(65) Prior Publication Data

US 2009/0299470 A1   Dec. 3, 2009

Related U.S. Application Data

(60) Provisional application No. 61/052,016, filed on May 9, 2008.

(51) Int. Cl.
*A61F 2/24* (2006.01)
(52) U.S. Cl. ...................... 623/2.36; 623/2.37
(58) Field of Classification Search .................. 623/2.36, 623/2.37
See application file for complete search history.

(56) References Cited

U.S. PATENT DOCUMENTS

| | | |
|---|---|---|
| 3,656,185 A | 4/1972 | Carpentier |
| 4,055,861 A | 11/1977 | Carpentier et al. |
| 4,164,046 A | 8/1979 | Cooley |
| 4,217,665 A | 8/1980 | Bex et al. |
| 4,602,911 A | 7/1986 | Ahmadi et al. |
| 5,041,130 A | 8/1991 | Cosgrove et al. |
| 5,061,277 A | 10/1991 | Carpentier et al. |

(Continued)

FOREIGN PATENT DOCUMENTS

EP   0 338 994   10/1989

(Continued)

OTHER PUBLICATIONS

Adams, David, et al., "Large Annuloplasty Rings Facilitate Mitral Valve Repair in Barlow's Disease," Society of Thoracic Surgeons 42$^{nd}$ Annual Meeting, Jan. 30-Feb. 1, 2006.

(Continued)

*Primary Examiner* — Thomas J Sweet
*Assistant Examiner* — Jason-Dennis Stewart
(74) *Attorney, Agent, or Firm* — AnneMarie Kaiser; Guy L. Cumberbatch

(57) ABSTRACT

A holder for an annuloplasty ring having a template defining a proximal face opposite the distal face, and a peripheral edge about which the annuloplasty ring conforms. The annuloplasty ring anchors to the template using one or more flexible filaments. The template includes a single cutting well on its proximal face over which the flexible filament is suspended. Desirably, the single cutting well is located adjacent the peripheral edge so as to be away from any handle connections for ease of access. The flexible filament emerges above the proximal face of the template at only one location at the cutting well, thus presenting a one cut quick-release structure that is highly visible to the surgeon. The annuloplasty ring may have a relatively rigid inner core surrounded by a suture-permeable cover, and the peripheral edge may be formed by a lower axial wall and an upper radial ledge that projects outward from the rigid inner core but not quite as far as a sewing margin of the ring. The ring and holder may be for mitral annuloplasty rings and generally have a D shape in plan view, and may be three-dimensional with upward anterior and posterior bows.

21 Claims, 10 Drawing Sheets

U.S. PATENT DOCUMENTS

| | | | |
|---|---|---|---|
| 5,064,431 | A | 11/1991 | Gilbertson et al. |
| 5,104,407 | A | 4/1992 | Lam et al. |
| 5,201,880 | A | 4/1993 | Wright et al. |
| 5,258,021 | A | 11/1993 | Duran |
| 5,306,296 | A | 4/1994 | Wright et al. |
| 5,496,336 | A | 3/1996 | Cosgrove et al. |
| 5,593,435 | A | 1/1997 | Carpentier et al. |
| 5,607,471 | A | 3/1997 | Seguin et al. |
| 5,674,279 | A | 10/1997 | Wright et al. |
| 5,776,189 | A | 7/1998 | Khalid |
| 5,824,066 | A | 10/1998 | Gross |
| 5,888,240 | A | 3/1999 | Carpentier et al. |
| 5,972,030 | A | 10/1999 | Garrison et al. |
| 6,102,945 | A | 8/2000 | Campbell |
| 6,143,024 | A | 11/2000 | Campbell et al. |
| 6,159,240 | A | 12/2000 | Sparer et al. |
| 6,183,512 | B1 | 2/2001 | Howanec, Jr. et al. |
| 6,187,040 | B1 | 2/2001 | Wright |
| 6,217,610 | B1 | 4/2001 | Carpentier et al. |
| 6,231,602 | B1 | 5/2001 | Carpentier et al. |
| 6,250,308 | B1 | 6/2001 | Cox |
| 6,258,122 | B1 | 7/2001 | Tweden et al. |
| 6,319,280 | B1 | 11/2001 | Schoon |
| 6,332,893 | B1 | 12/2001 | Mortier et al. |
| 6,391,054 | B2 | 5/2002 | Carpentier et al. |
| 6,406,493 | B1 | 6/2002 | Tu et al. |
| 6,419,696 | B1 | 7/2002 | Ortiz et al. |
| 6,602,288 | B1 | 8/2003 | Cosgrove et al. |
| 6,602,289 | B1 | 8/2003 | Colvin et al. |
| 6,619,291 | B2 | 9/2003 | Hlavka et al. |
| 6,709,456 | B2 | 3/2004 | Langberg et al. |
| 6,718,985 | B2 | 4/2004 | Hlavka et al. |
| 6,719,786 | B2 | 4/2004 | Ryan et al. |
| 6,726,717 | B2 | 4/2004 | Alfieri et al. |
| 6,764,510 | B2 | 7/2004 | Vidlund et al. |
| 6,797,002 | B2 | 9/2004 | Spence et al. |
| 6,800,090 | B2 | 10/2004 | Alferness et al. |
| 6,802,860 | B2 | 10/2004 | Cosgrove et al. |
| 6,805,710 | B2 | 10/2004 | Bolling et al. |
| 6,805,711 | B2 | 10/2004 | Quijano et al. |
| 6,858,039 | B2 | 2/2005 | McCarthy |
| 6,918,917 | B1 | 7/2005 | Nguyen et al. |
| 6,921,407 | B2 | 7/2005 | Nguyen et al. |
| 6,942,694 | B2 | 9/2005 | Liddicoat et al. |
| 6,955,689 | B2 | 10/2005 | Ryan et al. |
| 6,966,924 | B2 | 11/2005 | Holmberg |
| 6,986,775 | B2 | 1/2006 | Morales et al. |
| 7,101,395 | B2 | 9/2006 | Tremulis et al. |
| 7,118,595 | B2 | 10/2006 | Ryan et al. |
| 7,125,421 | B2 | 10/2006 | Tremulis et al. |
| 7,166,126 | B2 | 1/2007 | Spence et al. |
| 7,166,127 | B2 | 1/2007 | Spence et al. |
| 7,294,148 | B2 | 11/2007 | McCarthy |
| 7,691,143 | B2 | 4/2010 | Wright |
| 2001/0010018 | A1* | 7/2001 | Cosgrove et al. ............ 623/2.11 |
| 2003/0033009 | A1 | 2/2003 | Gabbay |
| 2003/0040793 | A1 | 2/2003 | Marquez |
| 2004/0249452 | A1 | 12/2004 | Adams et al. |
| 2004/0249453 | A1 | 12/2004 | Cartledge et al. |
| 2005/0131533 | A1 | 6/2005 | Alfieri et al. |
| 2005/0182487 | A1* | 8/2005 | McCarthy et al. ........... 623/2.11 |
| 2005/0256567 | A1 | 11/2005 | Lim et al. |
| 2005/0256568 | A1 | 11/2005 | Lim et al. |
| 2005/0267572 | A1 | 12/2005 | Schoon et al. |
| 2005/0278022 | A1 | 12/2005 | Lim |
| 2006/0015178 | A1 | 1/2006 | Moaddeb et al. |
| 2006/0015179 | A1 | 1/2006 | Bulman-Fleming et al. |
| 2006/0020336 | A1 | 1/2006 | Liddicoat |
| 2006/0025858 | A1 | 2/2006 | Alameddine |
| 2006/0030885 | A1 | 2/2006 | Hyde |
| 2007/0162111 | A1 | 7/2007 | Fukamachi et al. |
| 2009/0192602 | A1 | 7/2009 | Kuehn |
| 2009/0192603 | A1 | 7/2009 | Ryan |
| 2009/0192604 | A1 | 7/2009 | Gloss |
| 2009/0192606 | A1 | 7/2009 | Gloss et al. |
| 2010/0030329 | A1* | 2/2010 | Frater .......................... 623/2.36 |

FOREIGN PATENT DOCUMENTS

| | | |
|---|---|---|
| EP | 1 034 753 | 9/2000 |
| WO | WO 98/14138 | 4/1998 |
| WO | WO 99/49816 | 10/1999 |
| WO | WO 01/08608 | 2/2001 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons 31$^{st}$ Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

International Search Report from corresponding PCT Application No. PCT/US2009/043359 dated Aug. 4, 2009.

Brochure of "Cosgrove-Edwards Annuloplasty System," 2000.

"Minimally Invasive Mitral Valve Surgery," Navia, Dept of Thoracic and CardioThoracic Surgery, The Cleveland Clinic Foundation, Cleveland, OH, http://www.fac.org.ar/seve/llave/surgery/navia/naviai.htm.

\* cited by examiner

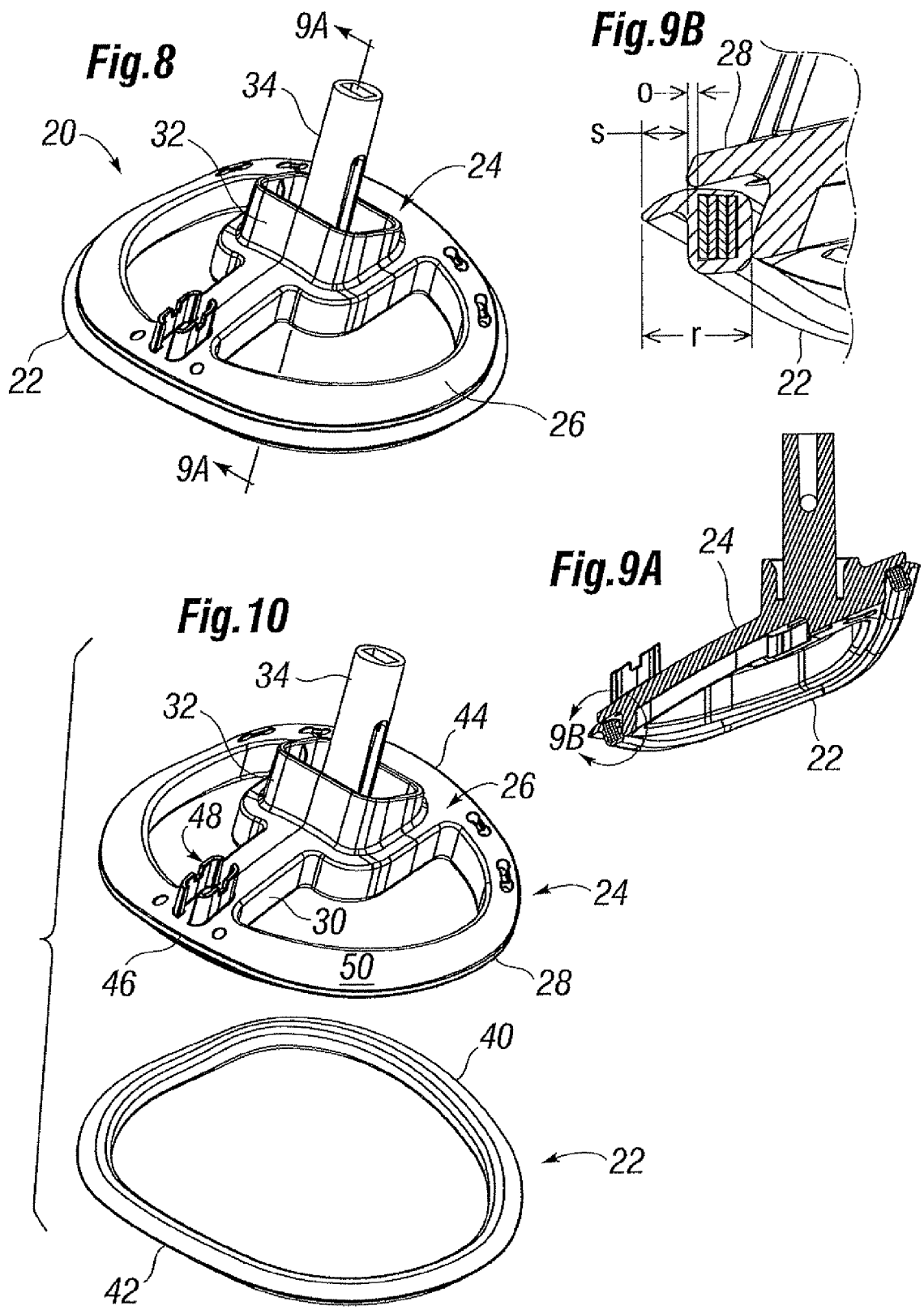

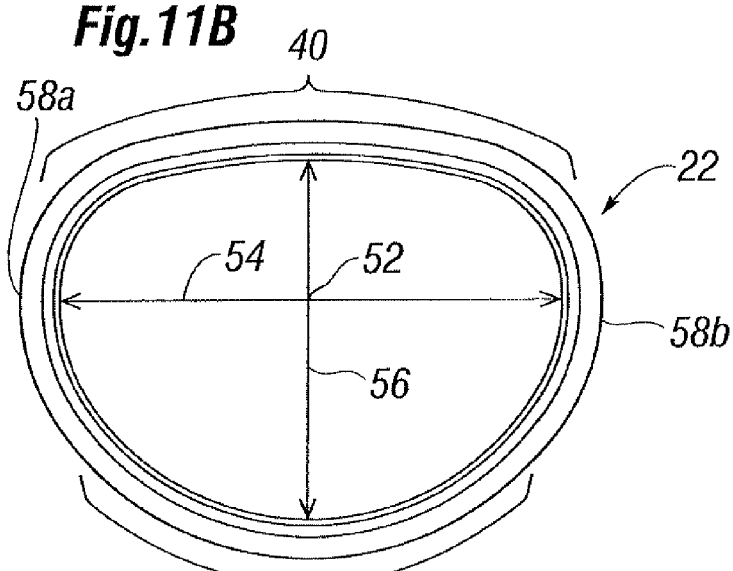
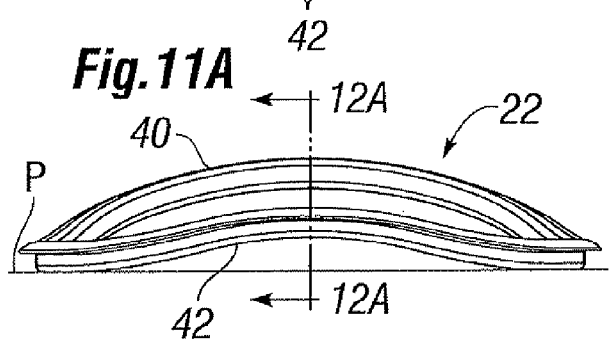
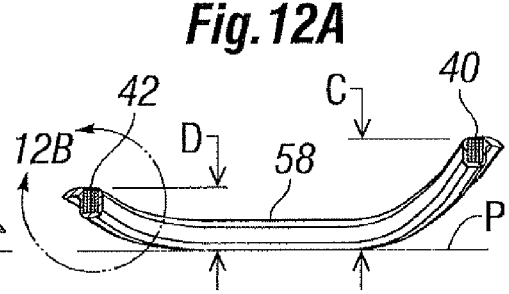
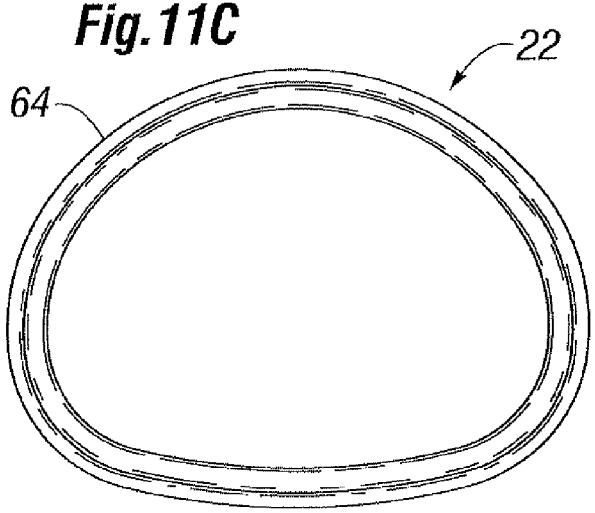
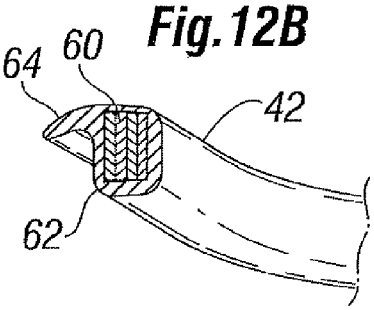

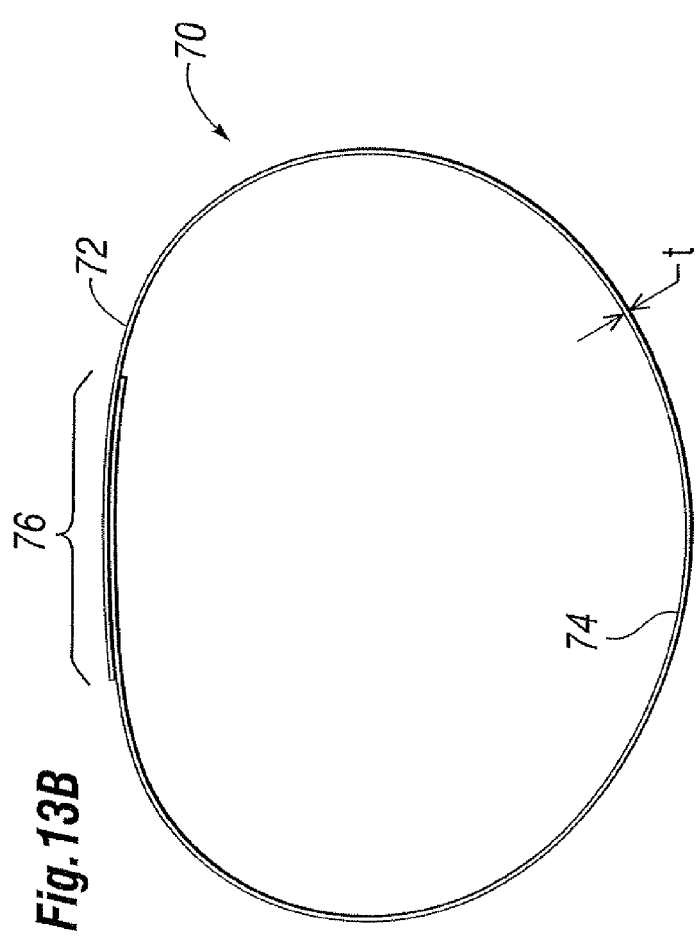
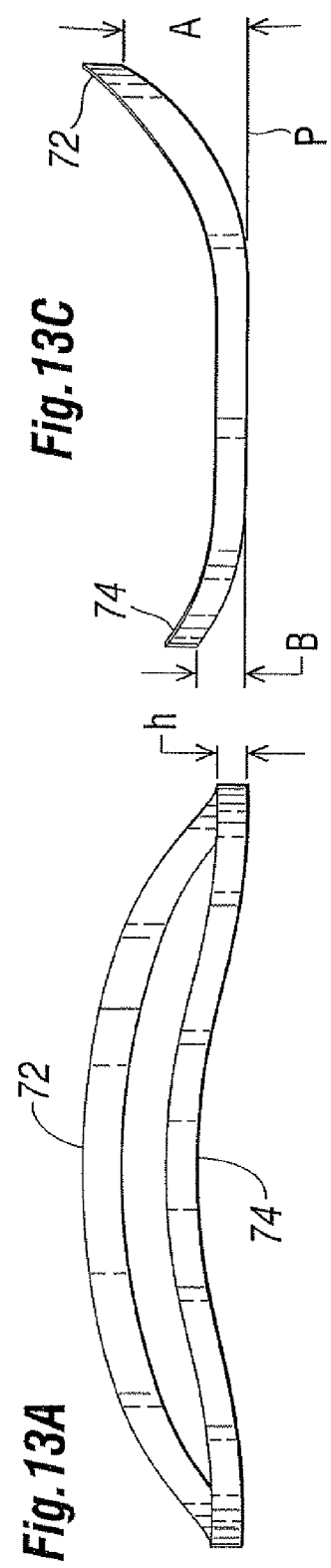
Fig. 13B
Fig. 13A
Fig. 13C

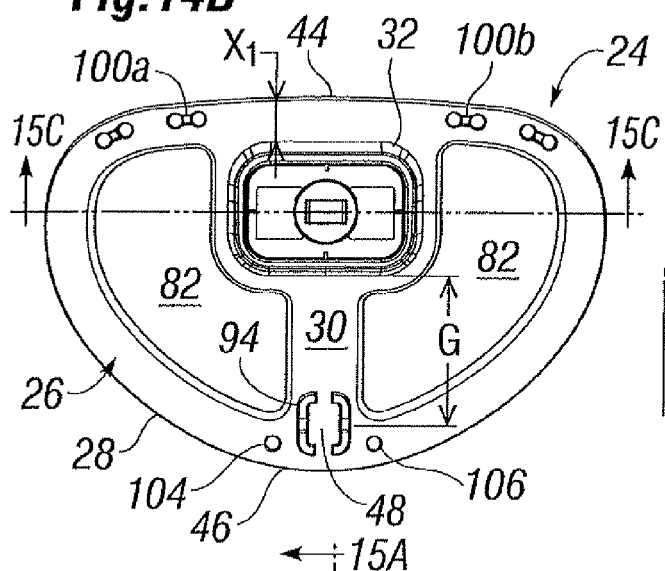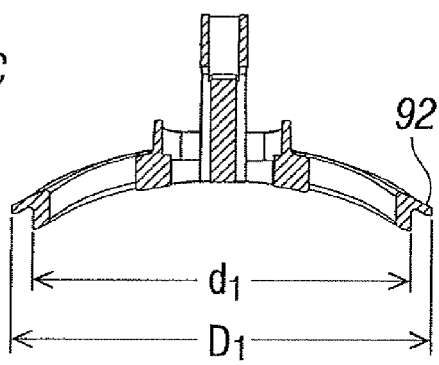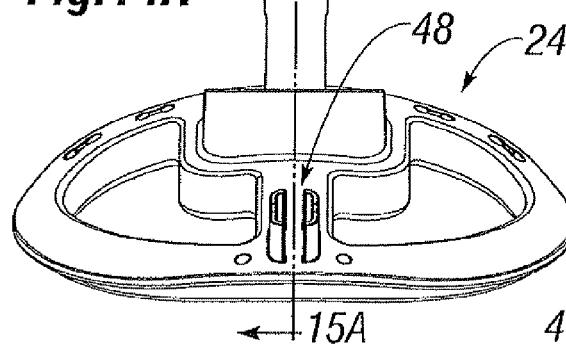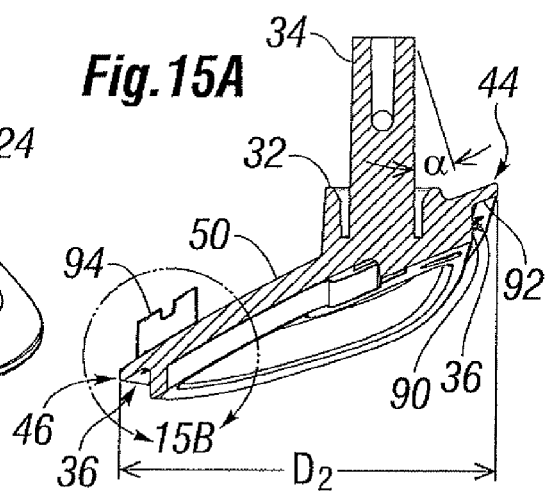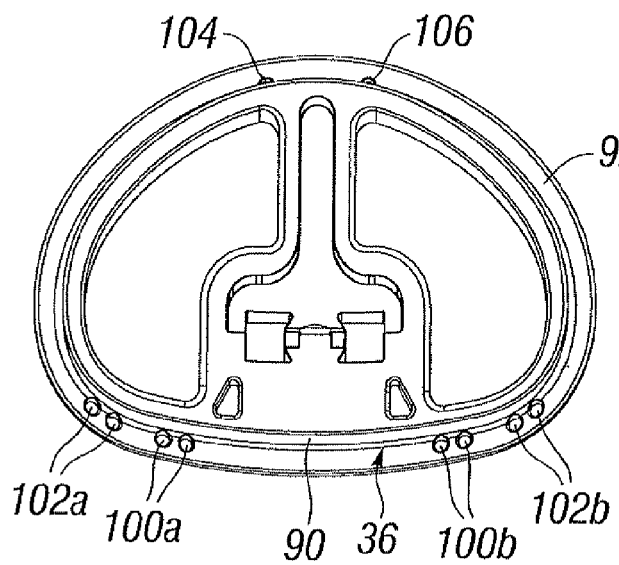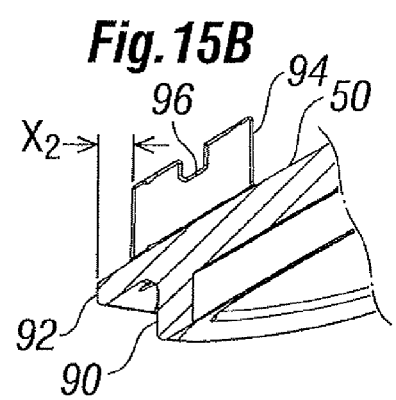

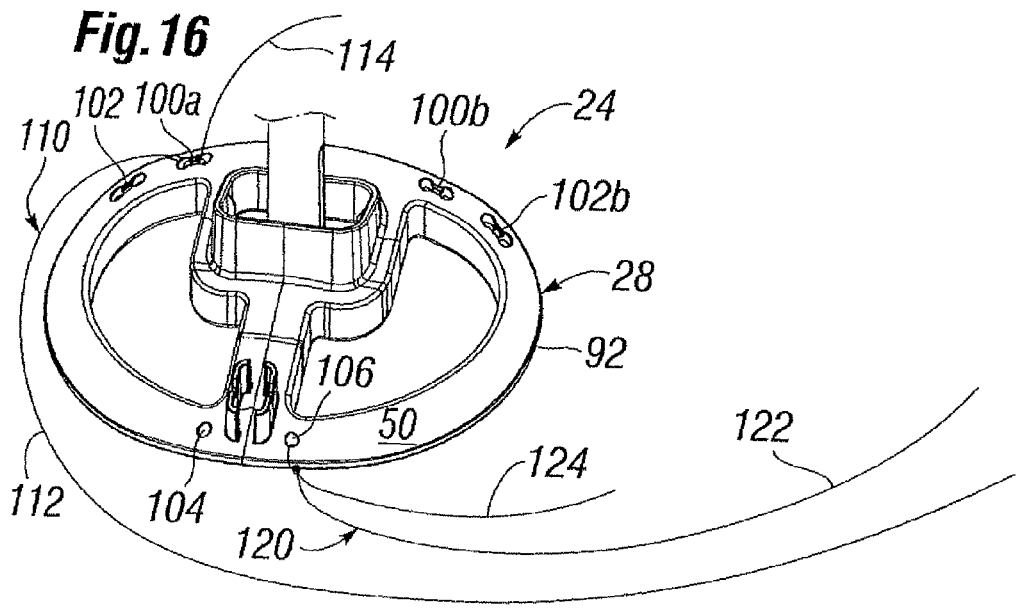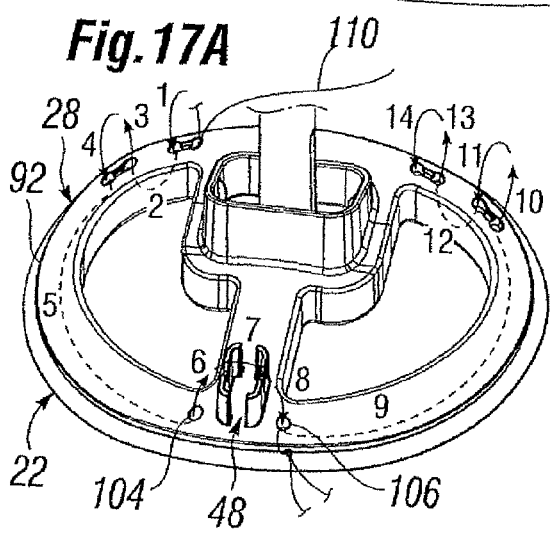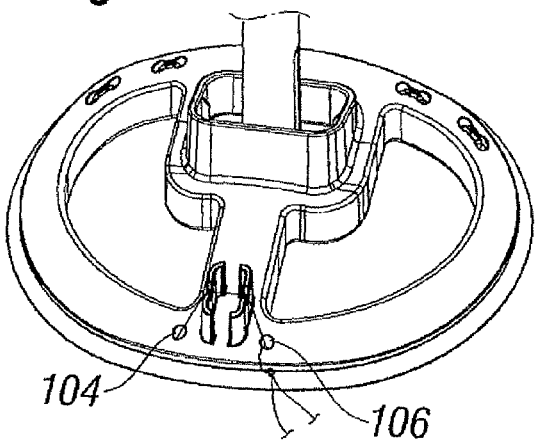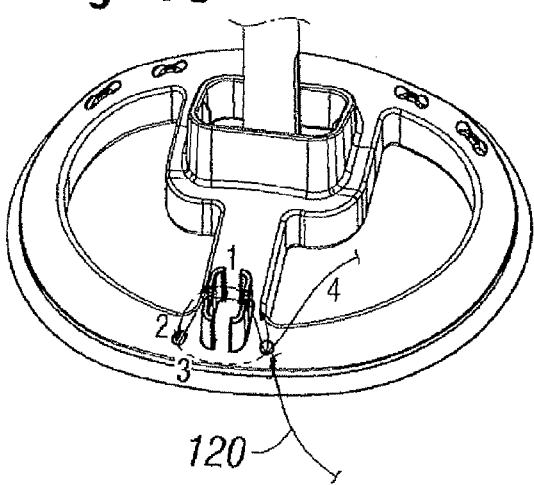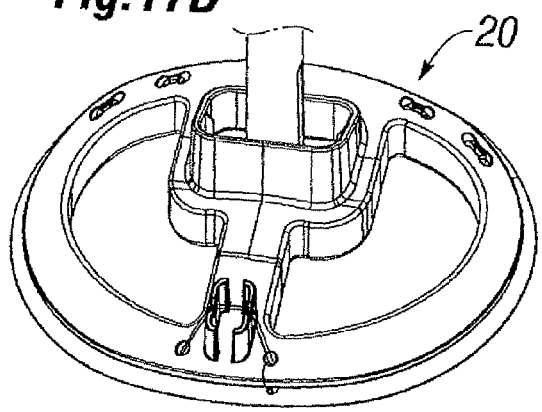

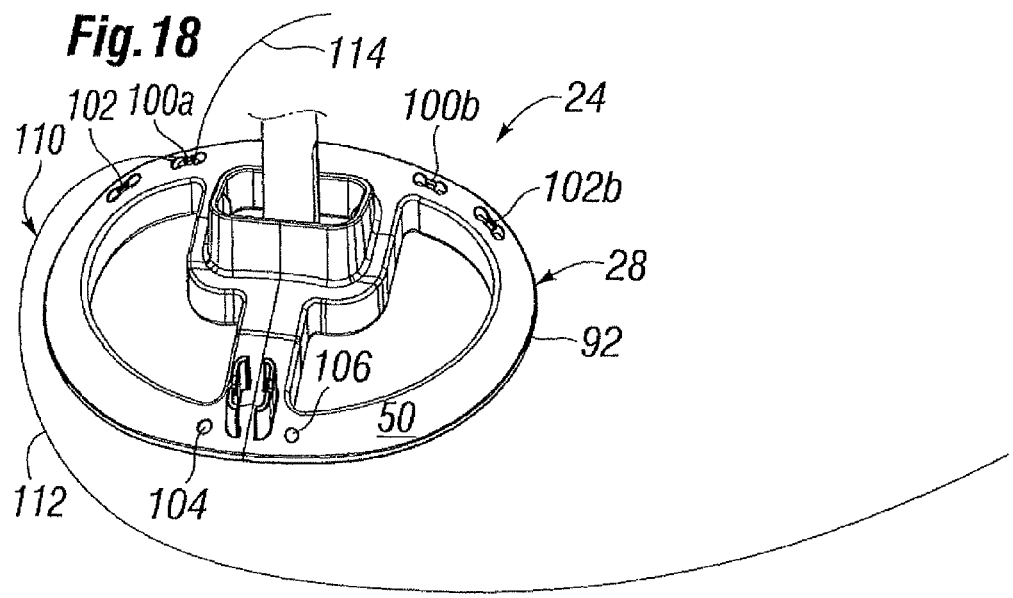
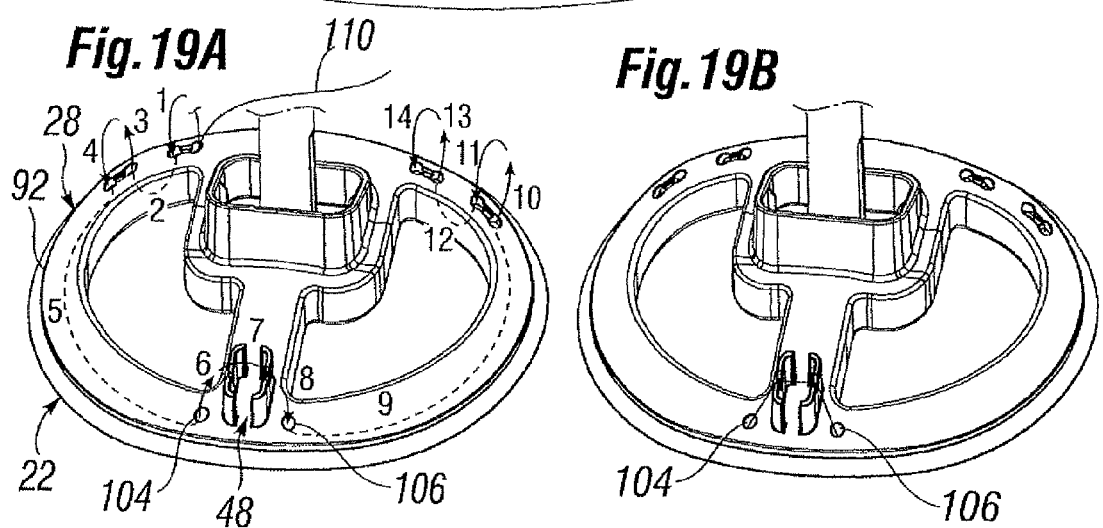
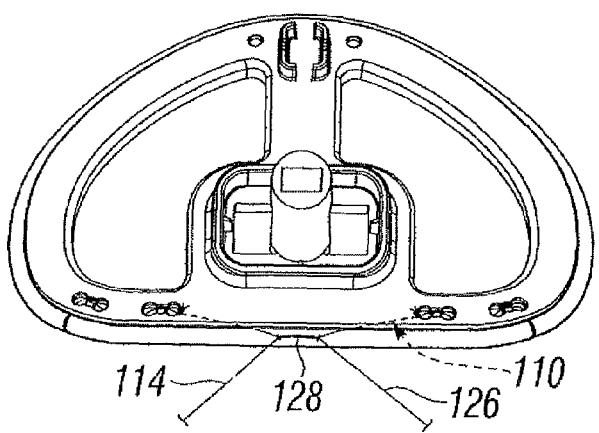

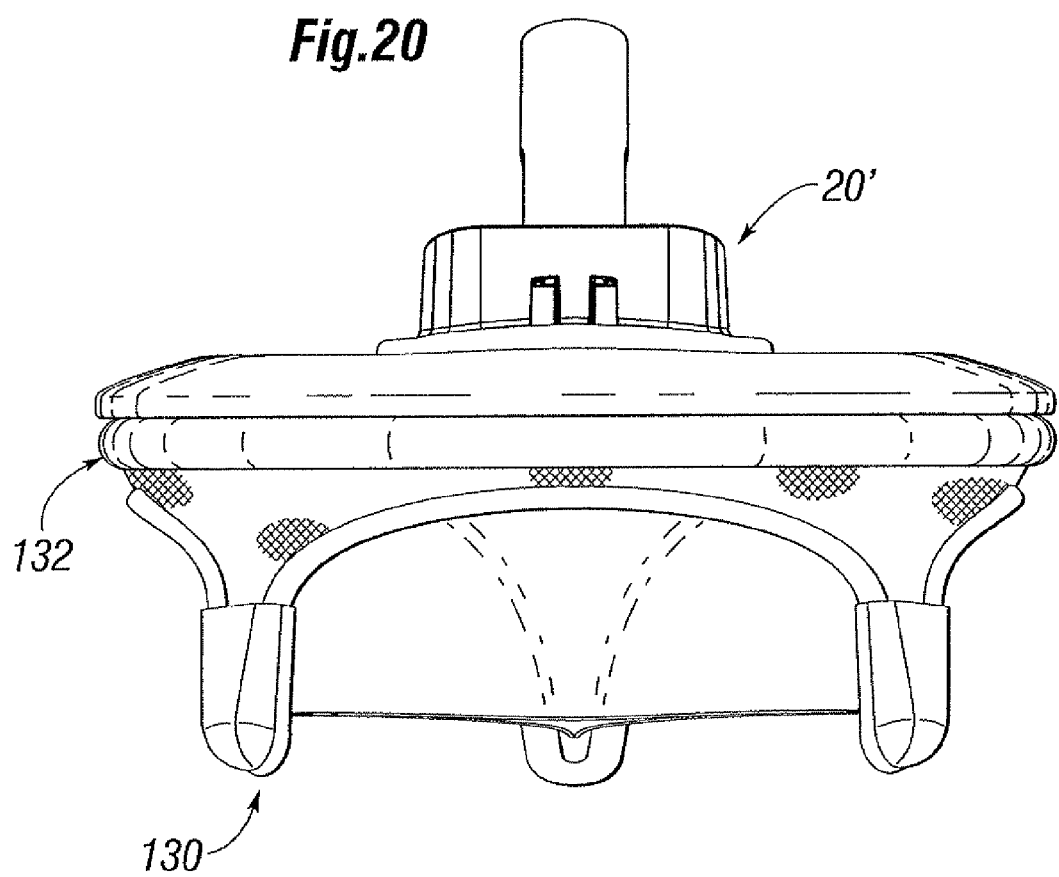

QUICK-RELEASE ANNULOPLASTY RING HOLDER

CROSS-REFERENCE TO RELATED APPLICATION

The present application claims priority to U.S. Provisional Application No. 61/052,016, filed May 9, 2008, which is incorporated herein by reference.

FIELD OF THE INVENTION

The present invention relates generally to holders for medical implants, and particularly to a holder for an annuloplasty ring, especially a mitral annuloplasty ring.

BACKGROUND OF THE INVENTION

In vertebrate animals, the heart is a hollow muscular organ having four pumping chambers as seen in FIG. 1: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atriums are the blood-receiving chambers, which pump blood into the ventricles. The ventricles are the blood-discharging chambers. A wall composed of fibrous and muscular parts, called the interatrial septum separates the right and left atriums (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

The mitral and tricuspid valves are defined by fibrous rings of collagen, each called an annulus, which forms a part of the fibrous skeleton of the heart. The annulus provides peripheral attachments for the two cusps or leaflets of the mitral valve (called the anterior and posterior cusps) and the three cusps or leaflets of the tricuspid valve. The free edges of the leaflets connect to chordae tendineae from more than one papillary muscle, as seen in FIG. 1. In a healthy heart, these muscles and their tendinous chords support the mitral and tricuspid valves, allowing the leaflets to resist the high pressure developed during contractions (pumping) of the left and right ventricles.

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (see FIGS. 5 and 6), the dimensions of the mitral valve annulus create an anatomic shape and tension such that the leaflets coapt, forming a tight junction, at peak contraction pressures. Where the leaflets coapt at the opposing medial and lateral sides of the annulus are called the leaflet trigones or commissures. The posterior leaflet is divided into three scallops or cusps, sometimes identified as P1, P2, and P3, starting from the anterior commissure and continuing in a counterclockwise direction to the posterior commissure. The posterior scallops P1, P2, and P3 circumscribe particular arcs around the periphery of the posterior aspect of the annulus, and the magnitude of those arcs vary depending on a variety of factors, including actual measurement of the mitral valve posterior leaflet scallops, and surgeon preference. As a rule, however, a major axis of the mitral annulus intersects both the first and third posterior scallops P1 and P3, and a minor axis intersects the middle posterior scallop P2.

Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease.

From a number of etiologies, mitral valve dysfunction can occur when the leaflets do not coapt at peak contraction pressures. As FIG. 7 shows, the coaptation line of the two leaflets is not tight at ventricular systole. As a result, an undesired back flow of blood from the left ventricle into the left atrium can occur.

Mitral regurgitation has two important consequences. First, blood flowing back into the atrium may cause high atrial pressure and reduce the flow of blood into the left atrium from the lungs. As blood backs up into the pulmonary system, fluid leaks into the lungs and causes pulmonary edema. Second, the blood volume going to the atrium reduces volume of blood going forward into the aorta causing low cardiac output. Excess blood in the atrium over-fills the ventricle during each cardiac cycle and causes volume overload in the left ventricle.

Mitral regurgitation is measured on a numeric Grade scale of 1+ to 4+ by either contrast ventriculography or by echocardiographic Doppler assessment, with 1+ being relatively trivial and 4+ indicating flow reversal into the pulmonary veins. In addition, mitral regurgitation is categorized into two main types, (i) organic or structural and (ii) functional. Organic mitral regurgitation results from a structurally abnormal valve component that causes a valve leaflet to leak during systole. Functional mitral regurgitation results from annulus dilation due to primary congestive heart failure, which is itself generally surgically untreatable, and not due to a cause like severe irreversible ischemia or primary valvular heart disease.

Organic mitral regurgitation is seen when a disruption of the seal occurs at the free leading edge of the leaflet due to a ruptured chord or papillary muscle making the leaflet flail; or if the leaflet tissue is redundant, the valves may prolapse the level at which coaptation occurs higher into the atrium with further prolapse opening the valve higher in the atrium during ventricular systole.

Functional mitral regurgitation occurs as a result of dilation of heart and mitral annulus secondary to heart failure, most often as a result of coronary artery disease or idiopathic dilated cardiomyopathy. Comparing a healthy annulus in FIG. 6 to an unhealthy annulus in FIG. 7, the unhealthy annulus is dilated and, in particular, the anterior-to-posterior distance along the minor axis (line P-A) is increased. As a result, the shape and tension defined by the annulus becomes less oval (see FIG. 6) and more round (see FIG. 7). This condition is called dilation. When the annulus is dilated, the shape and tension conducive for coaptation at peak contraction pressures progressively deteriorate.

The fibrous mitral annulus is attached to the anterior mitral leaflet in one-third of its circumference. The muscular mitral annulus constitutes the remainder of the mitral annulus and is attached to by the posterior mitral leaflet. The anterior fibrous mitral annulus is intimate with the central fibrous body, the two ends of which are called the fibrous trigones. Just posterior to each fibrous trigone is the commissure of which there are two, the anterior (or more accurately, the anterior medial), and the posterior (or posterior lateral). The commissures are where the anterior leaflet meets the posterior leaflet at the annulus.

As before described, the central fibrous body is also intimate with the non-coronary leaflet of the aortic valve. The central fibrous body is fairly resistant to elongation during the process of mitral annulus dilation. It has been shown that the great majority of mitral annulus dilation occurs in the posterior two-thirds of the annulus known as the muscular annulus. One could deduce thereby that, as the annulus dilates, the percentage that is attached to the anterior mitral leaflet diminishes.

In functional mitral regurgitation, the dilated annulus causes the leaflets to separate at their coaptation points in all phases of the cardiac cycle. Onset of mitral regurgitation may be acute, or gradual and chronic in either organic or in functional mitral regurgitation.

In dilated cardiomyopathy of ischemic or of idiopathic origin, the mitral annulus can dilate to the point of causing functional mitral regurgitation. It does so in approximately 25% of patients with congestive heart failure evaluated in the resting state. If subjected to exercise, echocardiography shows the incidence of functional mitral regurgitation in these patients rises to over fifty percent.

Functional mitral regurgitation is a significantly aggravating problem for the dilated heart, as is reflected in the increased mortality of these patients compared to otherwise comparable patients without functional mitral regurgitation. One mechanism by which functional mitral regurgitation aggravates the situation in these patients is through increased volume overload imposed upon the ventricle. Due directly to the leak, there is increased work the heart is required to perform in each cardiac cycle to eject blood antegrade through the aortic valve and retrograde through the mitral valve. The latter is referred to as the regurgitant fraction of left ventricular ejection. This is added to the forward ejection fraction to yield the total ejection fraction. A normal heart has a forward ejection fraction of about 50 to 70 percent. With functional mitral regurgitation and dilated cardiomyopathy, the total ejection fraction is typically less than thirty percent. If the regurgitant fraction is half the total ejection fraction in the latter group the forward ejection fraction can be as low as fifteen percent.

It is reported that 25% of the six million Americans who will have congestive heart failure will have functional mitral regurgitation to some degree. This constitutes the 1.5 million people with functional mitral regurgitation. Of these, the idiopathic dilated cardiomyopathy accounts for 600,000 people. Of the remaining 900,000 people with ischemic disease, approximately half have functional mitral regurgitation due solely to dilated annulus.

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

Currently, patient selection criteria for mitral valve surgery are very selective. Possible patient selection criteria for mitral surgery include: normal ventricular function, general good health, a predicted lifespan of greater than 3 to 5 years, NYHA Class III or IV symptoms, and at least Grade 3 regurgitation. Younger patients with less severe symptoms may be indicated for early surgery if mitral repair is anticipated. The most common surgical mitral repair procedure is for organic mitral regurgitation due to a ruptured chord on the middle scallop of the posterior leaflet.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. By interrupting the cycle of progressive functional mitral regurgitation, studies have shown increased survival and even increased forward ejection fraction in many surgical patients. The problem with surgical therapy is the significant insult it imposes on these chronically ill patients with high morbidity and mortality rates associated with surgical repair.

Surgical edge-to-edge juncture repairs, which can be performed endovascularly, are also made, in which a mid-valve leaflet to mid-valve leaflet suture or clip is applied to keep these points of the leaflet held together throughout the cardiac cycle. Other efforts have developed an endovascular suture and a clip to grasp and bond the two mitral leaflets in the beating heart. Grade 3+ or 4+ organic mitral regurgitation may be repaired with such edge-to-edge technologies. This is because, in organic mitral regurgitation, the problem is not the annulus but in the central valve components. However, functional mitral regurgitation can persist at a high level, even after edge-to-edge repair, particularly in cases of high Grade 3+ and 4+ functional mitral regurgitation. After surgery, the repaired valve may progress to high rates of functional mitral regurgitation over time.

In yet another emerging technology, the coronary sinus is mechanically deformed through endovascular means applied and contained to function solely within the coronary sinus.

One repair technique that has been shown to be effective in treating incompetence is annuloplasty, or reconstruction of the ring (or annulus) of an incompetent cardiac valve. The repair may be done entirely surgically, by cutting out a segment of leaflet and re-attaching the cut sides with sutures.

However, more typically the annulus is reshaped by attaching a prosthetic annuloplasty repair segment or ring thereto. For instance, the goal of a posterior mitral annulus repair is to bring the posterior mitral leaflet forward toward to the anterior leaflet to better allow coaptation. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate or core of a metal such as a rod or multiple bands of stainless steel or titanium, or a flexible material such as silicone rubber or Dacron cordage, covered with a biocompatible fabric or cloth to allow the ring to be sutured to the fibrous annulus tissue. More rigid cores are typically surrounded by an outer cover of both silicone and fabric as a suture-permeable anchoring margin. Annuloplasty rings may be stiff or flexible, split or continuous, and may have a variety of shapes in plan view, including circular, D-shaped, C-shaped, or kidney-shaped. Examples are seen in U.S. Pat. Nos. 5,041,130, 5,104,407, 5,201,880, 5,258,021, 5,607,471 and, 6,187,040.

One of the most frequently used is the partially flexible Carpentier-Edwards Physio® ring available from Edwards Lifesciences of Irvine, Calif. The Physio ring is a "semi-rigid" ring because it offers selective flexibility at the posterior section while preserving the remodeling effect through a rigid anterior section. Studies have shown that successful repair of an annulus is accomplished by remodeling the annulus using a rigid annuloplasty ring, especially for mitral repair. Still, advantages were thought to exist in permitting some flexibility, and semi-rigid rings provide a hybrid of the benefits of rigid rings and accommodation of annulus movement in one area such as the posterior side of mitral rings. Flexible rings are indicated for certain conditions, but do not perform a remodeling annuloplasty given their inherent lack of rigidity.

Most rigid and semi-rigid annular rings for the mitral valve have a kidney-like or D shape, with a relatively straight anterior segment co-extensive with the anterior valve leaflet, and a curved posterior segment co-extensive with the posterior valve leaflet. The shape of the annular rings reproduces the configuration of the valve annulus during the ventricular systole, and therefore in the stage of the valve closing. The ratio between minor axis and major axis is typically 3:4 in most models currently on the market since it reproduces normal anatomical ratios. Most of the earlier mitral rings were planar, while some (e.g., U.S. Pat. Nos. 5,104,407, 5,201,880, and 5,607,471) are bowed upward on their anterior segment (and slightly on their posterior segment) to accommodate the three-dimensional saddle shape of the anterior aspect of the mitral annulus. Newer rings have larger posterior bows (e.g., U.S. Pat. Nos. 6,805,710 and 6,858,039), or other three-dimensional configurations. Because of the variations in size and shape of the leaflets, particularly the anterior leaflets, it is frequently necessary to use an open rigid ring, such as the Carpentier-Edwards Classic® ring, also from Edwards Lifesciences, and modify its shape and dimensions by bending its extremities in order to accommodate the geometry of the anterior leaflet. Not all physicians agree which ring is appropriate for any one condition.

Correction of the aortic annulus requires a much different ring than for a mitral annulus. For example, U.S. Pat. Nos. 5,258,021 and 6,231,602 disclose sinusoidal or so-called "scalloped" annuloplasty rings that follow the up-and-down shape of the three cusp aortic annulus. Such rings would not be suitable for correcting a mitral valve deficiency.

In the usual mitral annuloplasty ring implant procedure, an array of separate implant sutures are first looped through all or portions of the exposed mitral annulus at intervals spaced equidistant from one another, such as for example 4 mm intervals. The surgeon then threads the implant sutures through the annuloplasty ring at more closely spaced intervals, such as for example 2 mm. This occurs with the prosthesis outside the body, typically secured to a peripheral edge of a holder or template. Despite the advantage of increases visibility, instances of snagging of the inner core with the implant sutures have occurred.

The ring on the holder is then advanced (parachuted) distally along the array of pre-anchored implant sutures into contact with the valve annulus, thus effecting a reduction in valve annulus circumference. At this point a handle used to manipulate the holder or template is typically detached for greater visibility of the surgical field. The surgeon ties off the implant sutures on the proximal side of the ring, and releases the ring from the holder or template, typically by severing connecting sutures at a series of cutting guides. Although sutures are typically used, other flexible filaments to connect the ring to the holder may be suitable. Because of the presence of multiple implant and connecting sutures in the surgical fields, the step of disconnecting the ring from the holder with a scalpel is somewhat delicate, and can be confusing for the novice. It should be noted that a similar holder connection and implant procedure, with attendant drawbacks, are also common for implanting prosthetic valves.

Despite numerous designs presently available or proposed in the past, there is a need for an improved holder for annuloplasty rings and prosthetic valves that will facilitate release of the prosthesis from the holder and help prevent snagging of any structural core with implant sutures.

SUMMARY OF THE INVENTION

The present invention provides an annuloplasty ring and holder assembly, comprising an annuloplasty ring including a suture-permeable outer cover and a template. The template has an upper, proximal face and a lower, distal face and a peripheral edge sized and adapted to receive the annuloplasty ring in conformal contact therewith. The template further includes a single cutting well adjacent the peripheral edge defined by a pair of spaced apart walls extending upward from the proximal face, and two spaced cleats adjacent the template peripheral edge each positioned at least 90° circumferentially around the peripheral edge from the cutting well. A flexible connecting filament has its free ends anchored to the two spaced cleats and a mid-portion passing through at least two points on the annuloplasty ring outer cover and emerging above the proximal face of the template at only one location where it is suspended across the cutting well. In this way, the task of severing the template from the ring is rendered extremely easy.

The annuloplasty ring desirably includes a generally rigid inner core surrounded by the suture-permeable outer cover. The template peripheral edge may be partly formed by an outwardly extending proximal ledge defining an outer extent of the template, wherein the proximal ledge extends radially outward from the rigid inner core when the annuloplasty ring is received in conformal contact with the peripheral edge and the suture-permeable outer cover extends outward from the proximal ledge.

Another aspect of the invention is an annuloplasty ring holder, comprising a template having an upper, proximal face and a lower, distal face and a peripheral edge sized and adapted to receive an annuloplasty ring in conformal contact therewith. The template further includes a single flexible connecting filament cutting well adjacent the peripheral edge defined by a pair of spaced apart walls extending upward from the proximal face, wherein the template further includes a coupler to which a handle member connects, and the coupler is located adjacent the peripheral edge diametrically opposite the cutting well.

An aspect of the present invention is method of delivering an annuloplasty ring to a target annulus. The method includes preparing an annuloplasty ring and template assembly for delivery. The template has an upper, proximal face and a lower, distal face and a peripheral edge sized and adapted to receive the annuloplasty ring in conformal contact therewith. The template further includes a single cutting well adjacent the peripheral edge defined by a pair of spaced apart walls extending upward from the proximal face. A flexible connecting filament anchored to the template holds the annuloplasty ring against the peripheral edge and bridges the cutting well. The template further including a coupler on the peripheral face to which a handle member connects, and the coupler is located adjacent the peripheral edge diametrically opposite the cutting well. A handle member is connected to the coupler, and the annuloplasty ring and template assembly are distally advanced into proximity with the target annulus. The flexible connecting filament is then severed at the cutting well thus releasing the annuloplasty ring from the template with a single severing step.

A further aspect of the invention comprises a set of annuloplasty ring holders, each having a template with an upper, proximal face and a lower, distal face and a peripheral edge sized and adapted to receive the annuloplasty ring in conformal contact therewith. The peripheral edge defines a 3-dimensional contour, and templates for different sized rings have different contours proportionally.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 8 is a perspective view of an exemplary annuloplasty ring holder of the present invention with an annuloplasty ring mounted thereon;

FIGS. 9A and 9B are radial sectional views through the annuloplasty ring holder and ring of FIG. 8;

FIG. 10 is an exploded perspective of the annuloplasty ring holder and annuloplasty ring of FIG. 8;

FIGS. 11A-11C are elevational and plan views of an exemplary annuloplasty ring for mounting on the holders of the present invention;

FIGS. 12A and 12B are radial sectional views through the annuloplasty ring of FIGS. 11A-11C;

FIGS. 13A-13C are elevational and plan views of a single band of an exemplary internal ring core of the annuloplasty ring of FIGS. 11A-11C;

FIGS. 14A-14C are elevational and plan views of an exemplary annuloplasty ring holder of the present invention;

FIG. 15A is a vertical sectional view through the annuloplasty ring holder of FIGS. 14A-14C, taken along line 15A-15A of FIG. 14A;

FIG. 15B is an enlargement of a portion of FIG. 15A;

FIG. 15C is a sectional view through the annuloplasty ring holder of FIGS. 14A-14C, taken along line 15C-15C of FIG. 14B;

FIG. 16 is a perspective view showing an initial step in attaching an annuloplasty ring to the exemplary annuloplasty ring holder of the present invention, namely securing two connecting sutures;

FIGS. 17A-17D are perspective views showing several steps in the process of attaching the annuloplasty ring to the exemplary holder of the present invention, namely threading the connecting sutures through the holder and ring;

FIG. 18 is a perspective view showing an initial step in an alternative process for attaching an annuloplasty ring to the exemplary annuloplasty ring holder of the present invention using only one connecting suture;

FIGS. 19A-19C are perspective views showing several steps in the process of attaching the annuloplasty ring to the exemplary holder of the present invention threading a single connecting suture through the holder and ring; and FIG. 20 is an elevational view of a holder of the present invention attached to a prosthetic heart valve.

DETAILED DESCRIPTION OF THE PREFERRED EMBODIMENTS

Figure 1:
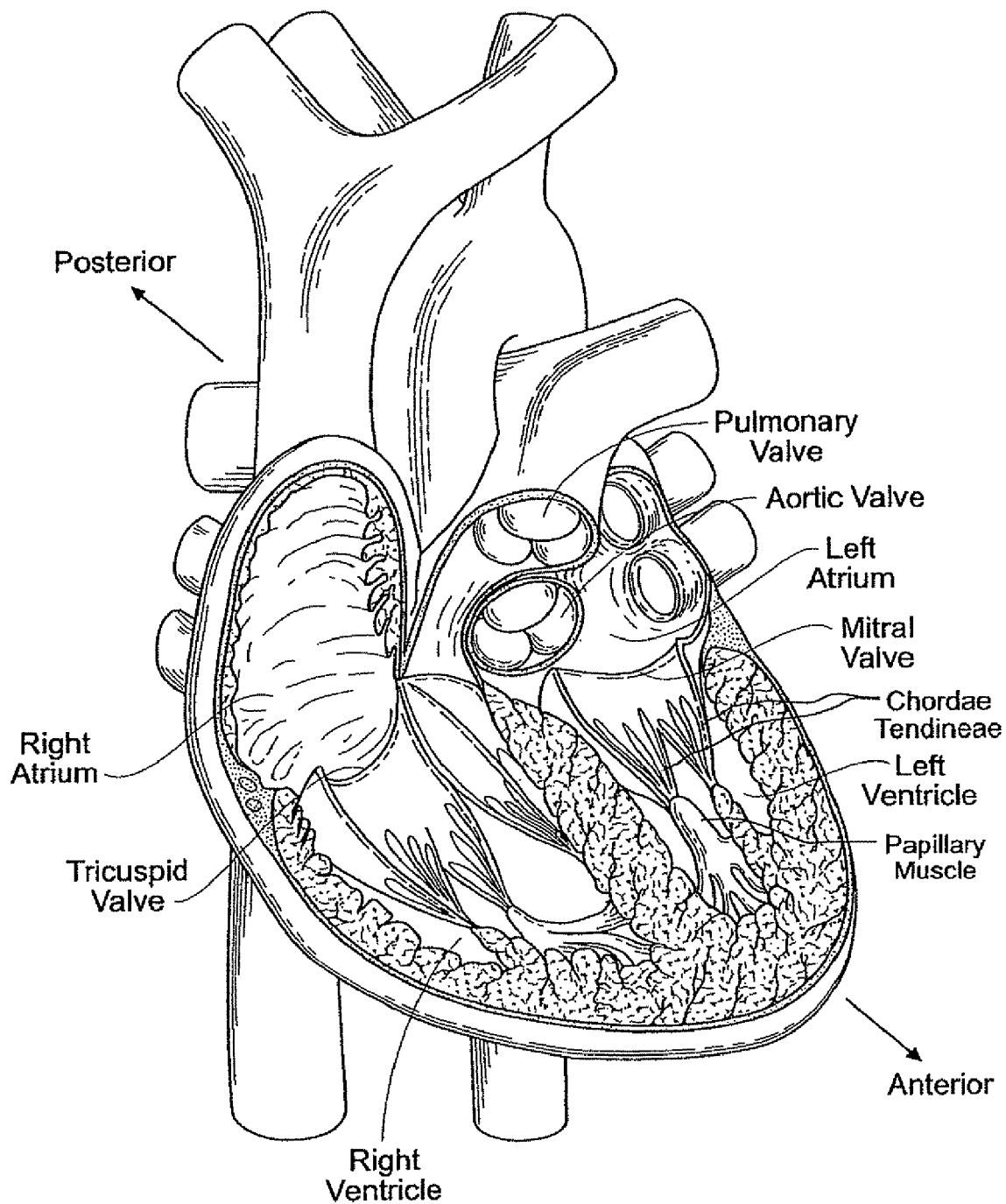
FIG. 1 is an anatomic anterior view of a human heart, with portions broken away and in section to view the interior heart chambers and adjacent structures.
Figure 2:
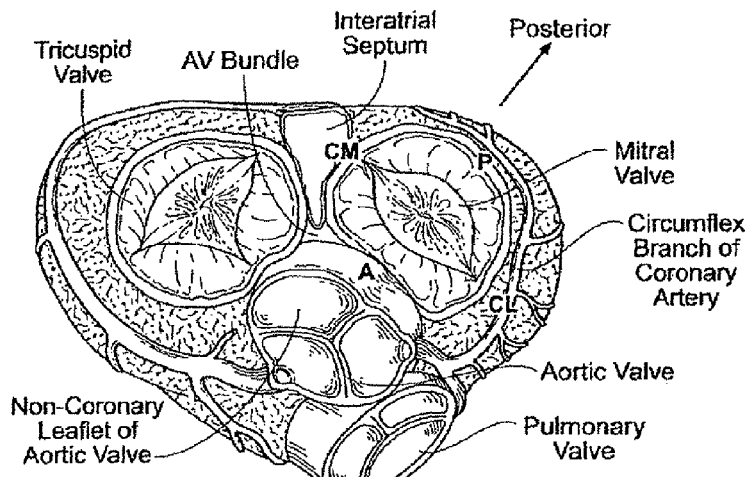
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 3:
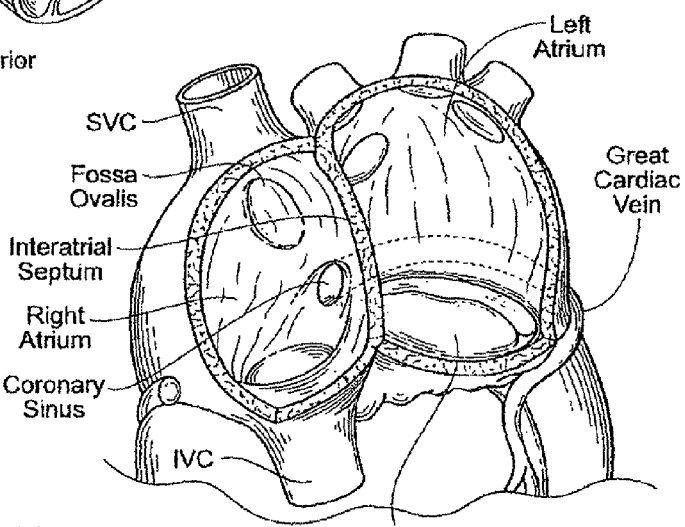
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.
Figure 4:
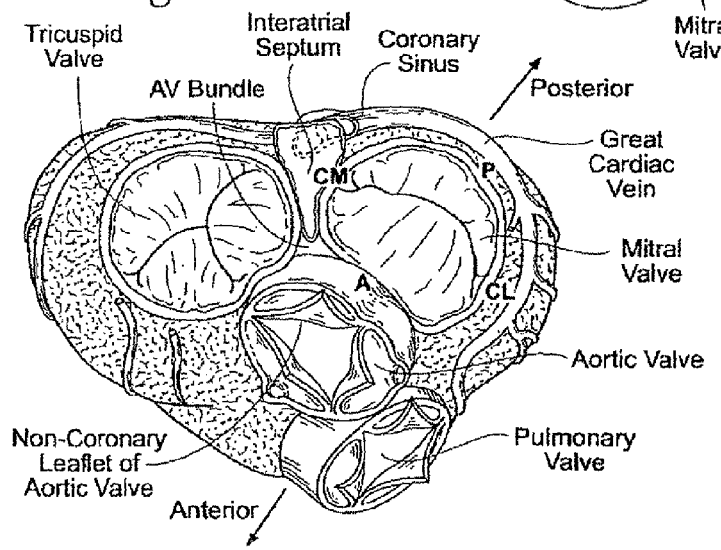
FIG. 4 is an anatomic anterior perspective view of the left and right atriums, with portions broken away and in section to show the interior of the heart chambers and associated structures, such as the fossa ovalis, coronary sinus, and the great cardiac vein.

The present invention provides an annuloplasty ring holder that facilitates an implant procedure. In particular, the holder of the present invention provides a quick-release cutting structure for severing connecting filaments between the holder and the annuloplasty ring. The surgeon need only to cut the connecting filaments at a single point. Moreover, the single cutting point is highly visible and located away from interfering structure on the holder.

The holder accommodates annuloplasty ring that are open or discontinuous (e.g., C-shaped) or closed or continuous (e.g., D-shaped). The ring can be rigid, flexible, or semi-flexible. The holders of the present invention can conform to planar or nonplanar rings, and are adaptable to rings used to repair any of the annuluses within the heart. Indeed, the holders of the present invention can even be utilized to hold heart valves, thus providing a quick release structure to separate the holder from the valve.

That said, the holders of the present invention are especially suitable for annuloplasty rings that are "generally rigid" and will resist distortion when subjected to the stress imparted thereon by the mitral valve annulus of an operating human heart. In this sense, "distortion" means substantial permanent deformation from a predetermined or manufactured shape. A number of "generally rigid" materials can be utilized as an inner core of the rings that will perform this function, including various bio-compatible polymers and metals and/or alloys. Certain polyesters that resist distortion and also rapid degradation within the body may be used (a material that degrades slowly may provide the required initial support). In a preferred embodiment, at least an inner core or body of the annuloplasty ring of the present invention is made of a suitable metal, such as ELGILOY® made by Elgiloy, L.P. of Elgin, Ill., U.S.A, or also titanium or its alloys. The core or ring body may be one piece, or may include a plurality of concentric or otherwise cooperating elements.

Furthermore, the annuloplasty ring holders of the present invention are also especially suited to hold annuloplasty rings designed to correcting particular pathologies. That is, holders may be provided for a set of rings defined by ring bodies wherein the proportional shapes of the ring bodies change with increasing nominal orifice sizes of the ring bodies in the set. The change of ring shape depends on the pathology being corrected. For instance, pathologies resulting in mitral regurgitation may benefit from a set of rings which have increasing circularity as the ring size increases. Such a set of rings are termed optimally-sized rings. It is important to understand that the set of rings include ring bodies that are formed during manufacture to be "generally rigid" and not easily manipulated. One example is a ring core formed of bands of Elgiloy® metal. A set of holders for such annuloplasty rings desirably has a peripheral shape that conforms to the optimally-sized rings. However, it should be understood that certain aspects of the holders of the present invention are also suitable for annuloplasty rings in general, not just optimally-sized rings.

The term "axis" in reference to the illustrated holders and rings, and other non-circular or non-planar holders and rings, refers to a line generally perpendicular to a specified center point of the holder periphery or ring when viewed in plan view. "Axial" or the direction of the "axis" can also be viewed as being parallel to the direction of blood flow within the valve orifice and thus within the ring when implanted therein. Stated another way, an implanted mitral ring orients about a central flow axis aligned along an average direction of blood flow through the mitral annulus. Although the holders and rings of the present invention may be 3-dimensional, certain features of the holders disclosed herein are also suitable for planar rings that lie generally perpendicular to the flow axis.

FIG. 8 illustrates an exemplary annuloplasty ring and holder assembly 20 of the present invention including an annuloplasty ring 22 mounted on a holder 24. As seen exploded in FIG. 10, the holder 24 comprises a template 26 defined by an outer peripheral edge 28 and a crossbar 30 extending from one side of the peripheral edge to another. The crossbar 30 widens on one side and provides a frame for a handle coupler 32 including an upstanding post 34. Although not shown, a handle member or intermediate cartridge may be attached to the coupling 32. The particular configuration of the coupler 32 may take the form of numerous well-known mechanical couplers. Desirably, the coupler 32 permits a handle member to be easily detached from the holder 24 so as to provide greater visibility during an implant procedure. The coupler 32 is located adjacent the anterior side of the peripheral edge 28.

FIGS. 9A and 9B are radial sectional views through the annuloplasty ring holder and ring assembly 20 of FIG. 8. As will be explained in greater detail below, the annuloplasty ring 22 conforms to an angled channel 36 (see FIG. 15B) defined by the peripheral edge 28, but extends radially outward from the channel. The annuloplasty ring 22 follows a three-dimensional path in the illustrated embodiment, and the peripheral edge 28 and channel mirror this three-dimensional shape. Further details on the structure of the annuloplasty ring 22 will be described below with respect to FIGS. 11-12.

With reference again to FIG. 10, the exemplary ring 22 and holder 24 are shown exploded. The annuloplasty ring 22 is designed for repair of the mitral annulus, and includes an anterior segment 40 opposite a posterior segment 42. Likewise, the template 26 defined an anterior segment 44 and a posterior segment 46. A single cutting well 48 projects upward from a proximal face 50 on the template 26, adjacent the posterior segment 46. The cutting well 48 is diametrically opposed across the template 26 from the coupler 32 and adjacent the peripheral edge 28.

The distance between the cutting well 48 adjacent the posterior segment 46 and the handle coupler 32 provides ample space for a surgeon to manipulate a cutting instrument within the surgical field. Moreover, the single cutting well 48 presents the only portion of a suture or filament connecting the ring 22 to the holder 24 that extends above the proximal face 50. This combination of features provides a one cut release structure that is highly visible to the surgeon. Indeed, the filament suspended across the cutting well 48 is essentially the only portion of the filament visible looking down on the proximal face 50. As will be seen in more detail below, there are several places where knots in the connecting filament can be seen from above the proximal face 50, but these are virtually points presenting no length of filament to cut.

The proximal face 50 of the template 26 desirably comprises a substantially smooth upper surface that extends at least around the peripheral edge 28. Certain features of the present invention are defined relative to the proximal face 50. For instance, some features are recessed below the proximal face 50, emerge above it, or are visible on the proximal face. However, the proximal face 50 is not a monolithic surface, nor is it planar. For the purpose of definition, the proximal face 50 is that surface that makes up the majority of the proximal side of the template 26 and is substantially smooth. Interruptions or discontinuities in the proximal face 50 may be readily apparent or not, depending on their relative size and projection above the proximal face 50. For instance, the single cutting well 48 projects relatively high above the proximal face 50 and is located near the peripheral edge 28 and opposite from the handle coupler 32 so as to highly visible. Certain other features, as will be explained below, may be exposed to the proximal side of the template but are relatively small and/or recessed in the proximal face 50 so as to be much less apparent, especially in the usually bloody environment of the surgical field.

FIGS. 11A-11C show the exemplary annuloplasty ring 22 that may be mounted on the holders of the present invention. FIG. 11A is an elevational view of the posterior side of the ring 22 illustrating that the anterior segment 40 in the rear rises to a greater elevation than the posterior segment 42 in front. The elevations referenced herein are relative to a datum plane P that lies perpendicular to a central axis 52 at the intersection of a major dimension 54 and a minor dimension 56 of the template 26, as illustrated in FIG. 11B. As will be clear, the dimensions 54, 56 are drawn between the projections of the anterior and posterior segments 40, 42 onto the datum plane, rather than directly between those segments, because they rise to different elevations. Also, although not labeled, the template 26 defines a major axis along the line of the major dimension 54, and a minor axis along the line of the minor dimension 56. The minor axis bisects the template 26 into two symmetric halves, while the major axis extends across the widest portion of the template, thus generally delineating anterior and posterior halves which are not symmetric. Although the template peripheral edge 28 is not circular, features and dimensions may be described herein as radially outward from the central axis 52.

With reference to FIG. 11B, the upper anterior segment 40 extends substantially across the straight portion of the ring 22, and generally corresponds to the dimension of an anterior mitral leaflet. In this respect, the anterior segment 40 is adapted to be implanted against the anterior aspect of the mitral annulus. In the anatomy of the mitral valve, the posterior leaflet extends around the remainder of the annulus, along a circumferential arc of greater than 180°, and the anterior and posterior leaflets meet at two commissures. Therefore, the anterior segment 40 has a length and shape that is designed to correspond to the anterior aspect of the mitral annulus between the two commissures.

While the anterior segment 40 corresponds to the anterior aspect, the remainder of the ring corresponds to the posterior aspect. The posterior segment 42 is shown in FIG. 11B centered on the side opposite the anterior segment 40, though not extending all the way around to the anterior segment 40. For purpose of definition, the posterior segment 42 will be defined as that portion of the ring 22 on the posterior side that rises up from the datum plane P.

Figure 5:
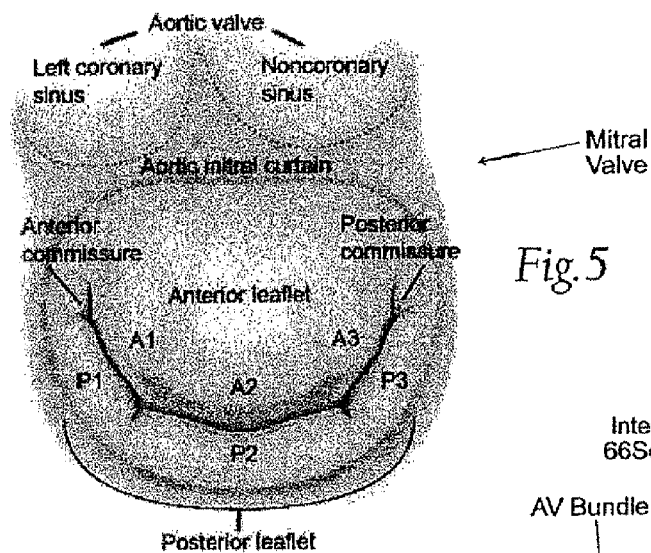
FIG. 5 is a superior view of a healthy mitral valve, with the leaflets closed and coapting at peak contraction pressures during ventricular systole and indicating the primary anatomical landmarks.
Figure 6:
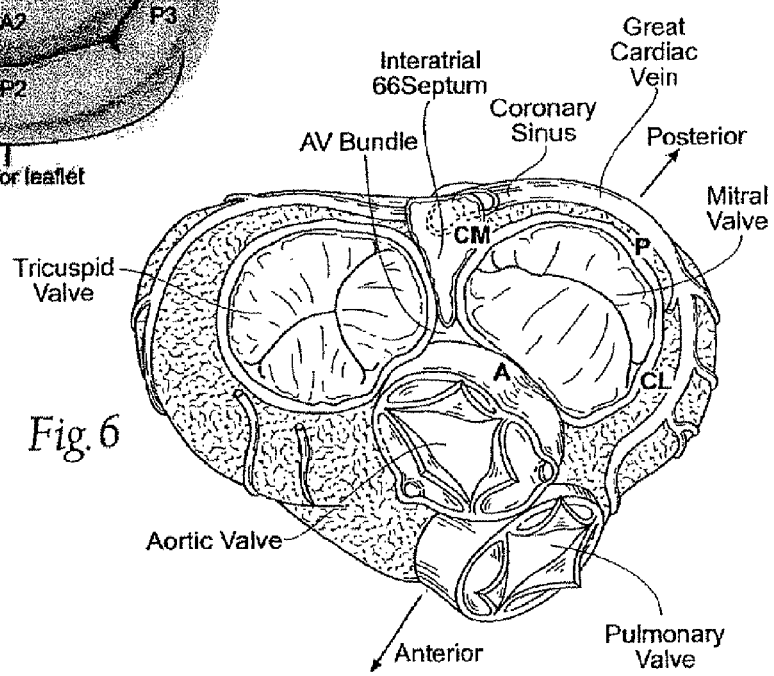
FIG. 6 is an anatomic superior view of a section of the human heart, with the normal mitral valve shown in FIG. 5 closed during ventricular systole (ventricular emptying) of the cardiac cycle.
Figure 7:
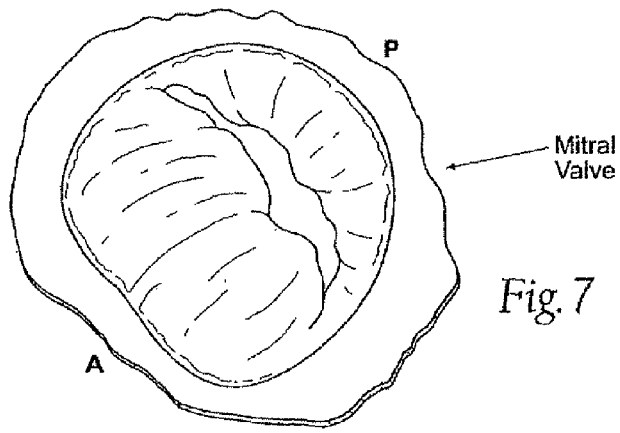
FIG. 7 is a superior view of a dysfunctional mitral valve, with the leaflets failing to coapt during peak contraction pressures during ventricular systole, leading to mitral regurgitation.

A left side segment 58a and a right side segment 58b thus connect the anterior segment 40 and posterior segment 42. The side segments 58a, 58b may be shaped with a continuous curve, so as to have a lower apex on the datum plane P, or may be coextensive with the datum plane P for a short distance as seen in FIG. 12A. In the latter configuration, therefore, the datum plane is defined by the plane in which the side segments 58a, 58b lie. Although not precise for all mitral valves, the segments around the ring 22 exclusive of the anterior segment 40 correspond generally to the three scallops of the posterior leaflet, as seen in FIG. 5. Namely, the left side segment 58a corresponds to the first posterior scallop P1, the right side segment 58b corresponds to the third posterior scallop P3, and the posterior segment 42 corresponds to the second posterior scallop P2. Also, the axis of the ring along the minor dimension 56 intersects the posterior segment 42, while the axis along the major dimension 54 intersects the left and right side segments 58a, 58b.

The general three-dimensional contours of the ring 22 are similar to a commercial ring sold by Edwards Lifesciences of Irvine, Calif. under the trade name Carpentier-Edwards Physio® Annuloplasty Ring, in that the anterior and posterior segments 40, 42 rise upward to create something of a "saddle" shape. However, the absolute heights to which the anterior and posterior segments 40, 42 rise are greater, and the preferred annuloplasty ring 22 is optimally sized. The holder 24 of the present invention can be easily modified to conform to the Physio® Ring, or any number of other rings for that matter. As mentioned above, a preferred annuloplasty ring 22 for use with the holder 24 also includes optimal sizing. Further details of the exemplary annuloplasty ring 22 are provided in U.S. application Ser. No. 12/028,714, filed Feb. 8, 2008, the disclosure of which is expressly incorporated herein.

In particular, optimally-sized rings have gradually increasing minor axis dimension 52 to major axis dimension 54 ratio (which may be termed "aspect ratio"). The dimensions 52 and 54 are measured to the inner edge of the ring 22. This increasing dimensional ratio provides rings in the larger sizes that are more suited to correcting conditions where the mitral leaflet is floppy, and in general for Type II pathologies such as infective endocarditis and floppy mitral valve. Typically, larger patients exhibit this general condition leading to regurgitation as opposed to smaller patients, for which rings having more conventional major/minor ratios are more appropriate.

The following table indicates the actual values of the major and minor axes as measured across the interior of the ring 22 (dimensions 54 and 52, respectively, in FIG. 11B) for nine different exemplary rings, and also gives the ratios of the minor axis to the major axis. The rings have nominal orifice sizes in even millimeter increments (e.g., 24 mm, 26 mm, etc.) as measured across the major axes. Such rings will have distinct packaging so as to be labeled with the particular size.

| Ring size (mm) | Major axis (mm) | Minor Axis (mm) | B/A ratio |
| --- | --- | --- | --- |
| 24 | 24.0 | 16.5 | 0.6875 |
| 26 | 26.0 | 17.7 | 0.6808 |
| 28 | 28.0 | 18.9 | 0.6750 |
| 30 | 30.0 | 20.4 | 0.6800 |
| 32 | 32.0 | 21.9 | 0.6844 |
| 34 | 34.0 | 23.5 | 0.6912 |
| 36 | 36.0 | 25.5 | 0.7083 |
| 38 | 38.0 | 28.5 | 0.7500 |
| 40 | 40.0 | 32.0 | 0.8000 |

A set of the exemplary holders 24 desirably conforms to the set of optimally-sized rings. That is, the templates 26 each has a peripheral edge 28 sized and adapted to receive an annuloplasty ring in conformal contact therewith, the peripheral edge of each ring preferably defining a 3-dimensional contour. For a set of optimally-sized rings, therefore, the templates 26 for different sized rings have different contours proportionally. For instance, the template 26 has an anterior segment 44 and a posterior segment 46, as seen in FIG. 10, and as indicated above the aspect ratio of larger rings may increase. The distance $D_1$ between the anterior and posterior segment 44, 46 therefore may increase relative to the distance $D_2$ across lateral dimension of the ring (see FIGS. 15A and 15C).

FIGS. 12A and 12B are radial sectional views through the annuloplasty ring 22 and illustrated a preferred inner construction. The annuloplasty ring 22 comprises a generally rigid inner core 60 surrounded by a suture-impermeable outer cover 62. Inner core 60 preferably includes a plurality of concentric bands each having a greater axial than radial dimension. One of the bands is shown in FIG. 13A-13C, and will be described in more detail below. As mentioned above, the inner core 60 may also be formed of a solid member and may be made of a variety of generally rigid materials, including in particular ELGILOY® made by Elgiloy, L.P. of Elgin, Ill., U.S.A, or titanium and its alloys. The outer cover 62 may comprise a number of materials, but a particular useful configuration is molded silicone surrounded by a fabric covering (not shown for clarity). One exemplary ring is constructed with ELGILOY® bands separated by polyester films strips, and has an outer cover 62 providing a sewing ring margin of a layer or tube of silicone rubber covered with a woven polyester cloth.

FIG. 12A shows preferred heights above a datum plane P, with the center of the anterior segment 40 rising to height C and the center of the posterior segment 42 rising to height D, with a desired ratio of C/D>1. The preferred ratio of C/D is about 3:1, with the smallest rings rising to a little more than 3 mm on the anterior side and the largest to about 6 mm.

The following table indicates exemplary values of the heights above the datum plane P of the anterior segment and the center of the posterior segment.

| Ring size (mm) | Anterior Height, C (mm) | Posterior Height, D (mm) |
|---|---|---|
| 24 | 3.6 | 1.4 |
| 26 | 3.9 | 1.6 |
| 28 | 4.2 | 1.7 |
| 30 | 4.7 | 1.9 |
| 32 | 5.0 | 2.0 |
| 34 | 5.3 | 2.1 |
| 36 | 5.8 | 2.3 |
| 38 | 6.1 | 2.4 |
| 40 | 6.4 | 2.6 |

It should be noted that the ratio of the heights of the opposite sides, anterior and posterior, changes with increasing nominal orifice size. The smallest ring, 24 mm, has a C/D ratio of 3.6/1.4, or about 2.57, while the largest ring, 40 mm, has a C/D ratio of 6.4/2.6, or about 2.46. The trend is for the C/D ratio to become smaller as the ring size increases. Although this ratio change may appear slight, more significant C/D ratio changes for certain degenerative conditions are also possible. Also, the trend may be opposite such that the larger rings have a greater C/D ratio than smaller rings, or in other words the anterior height relative to the posterior height becomes greater in larger rings. Therefore, optimally-sized rings encompass not only a change in proportional plan view shape, but a change in the anterior-posterior height ratio of the rings.

With reference to FIG. 12B, the outer cover 62 closely surrounds the core 60 and desirably includes a radially outwardly extending sewing margin 64. Therefore, if the core 60 is rectangular in cross-section as shown, the outer cover 62 includes a hollow rectangular portion and the outwardly projecting sewing margin 64. This sewing margin 64 is shown as a slightly curled lip or finger projecting from an upper or proximal side of the cover 62, but may also take the form of a more rounded bulge or other shapes.

FIGS. 13A-13C are elevational and plan views of a single band 70 of an exemplary internal ring core 60 of the annuloplasty ring 22 of the present invention. As mentioned above, the band has an axial height h that is significantly greater than its radial thickness t. Both the axial height h and the radial thickness t may be constant around the band 70 or may vary. In a preferred embodiment, the axial height h is slightly greater in an anterior segment 72 than in a posterior segment 74 of the band, while the radial thickness t remains constant. The band 70 further includes a section 76 in the anterior segment 72 where the free ends of the band overlap. By virtue of this overlap, as well as the slightly greater axial height h, the band 70 is less flexible in the anterior segment 72 than in the posterior segment 74.

A series of differently sized annuloplasty rings 22 are provided for different patients. By convention, the rings are labeled and identified by their major axis dimension in millimeters, typically in even 2 mm increments between 24-40 mm. It should be noted that the major axis dimension is used for the ring 22 in general, although the dimension typically corresponds to the inner dimension along the major axis of the inner core 60, thus communicating the major axis dimension of the orifice defined by the structural core of the ring. Therefore, for a 24 mm ring, for example, the inner band 70 will have a major dimension of about 0.945 inches (24 mm), while a 40 mm ring will have an inner band having a major dimension of about 1.575 inches (40 mm).

FIG. 13C illustrates the relative elevations of the anterior and posterior segments 72, 74. Namely, the center of the anterior segment 72 rises to a height A above a datum plane P, while the center of the posterior segment 74 rises to a lower height B above the datum plane P. Because the combination of the multiple bands 70 within the inner core 60 provides the structural rigidity within the annuloplasty ring 22, the combined shape of the bands defines the shape of the ring. In a preferred embodiment, there are four bands 70 having approximately the same shapes, with slightly different radial dimensions by virtue of their concentric arrangement.

The following table indicates exemplary values of the heights above a datum plane of the anterior segment 72 and the center of the posterior segment 74.

| Ring size (mm) | Anterior Height, 72 (mm) | Posterior Height, 74 (mm) |
|---|---|---|
| 24 | 3.6 | 1.4 |
| 26 | 3.9 | 1.6 |
| 28 | 4.2 | 1.7 |
| 30 | 4.7 | 1.9 |
| 32 | 5.0 | 2.0 |
| 34 | 5.3 | 2.1 |
| 36 | 5.8 | 2.3 |
| 38 | 6.1 | 2.4 |
| 40 | 6.4 | 2.6 |

The preferred ratio of the anterior height over the posterior height is between about 1.4:1 to 3:1, with the smallest rings rising to a little more than 3 mm on the anterior side and the largest to about 6 mm.

FIGS. 14A-14C are elevational and plan views of an exemplary annuloplasty ring holder 24 of the present invention shown without the annuloplasty ring 22. As mentioned above, holder 24 includes the template 26 defined by the peripheral edge 28 and a crossbar 30 and extending from one side of the peripheral edge to another. The peripheral edge 28 has the same shape in plan view as the annuloplasty ring 22 that it is designed to hold, thus is somewhat D-shaped and defines a major axis dimension and a minor axis dimension. The crossbar 30 extends along the minor axis dimension of the holder 24, with the coupler 32 located adjacent the peripheral edge 28 at the anterior segment 44 of the template 26. Between the peripheral edge 28 and the crossbar 30 template 26 provides a pair of relatively large visibility windows 82 that together occupy a majority of the cross-sectional area within the peripheral edge. The windows 82 allow the surgeon to see distally through the holder 24 and ring 22 to evaluate the condition of the mitral annulus as the ring is implanted. In a similar manner, if the holder 24 is utilized for holding a prosthetic valve, the windows 82 provide enhanced visibility of the prosthetic valve leaflet structure.

One advantage of the holder 24 of the present invention is the ability to release the annuloplasty ring 22 by cutting connecting suture(s) at a single highly visible location. At the same time, the connecting sutures firmly hold the annuloplasty ring 22 around the peripheral edge 28 to maintain the desired shape of the ring against the target annulus without movement during the implant procedure. An exemplary series of through holes for passage of the connecting filament relative to the single cutting well 48 is best seen in FIGS. 14B and 14C. Prior to explanation of those through holes, however, a better explanation of the peripheral edge configuration is appropriate.

As mentioned above, the annuloplasty ring 22 conforms to an angled channel 36 defined by the peripheral edge 28, but extends radially outward from the channel. FIGS. 15A-15C are sectional views through the annuloplasty ring holder 22 and show the angled channel 36 defined by a generally axially-extending distal wall 90 and an outwardly extending proximal ledge 92 forming an outer extent of the template. The distal wall 90 desirably extends in parallel with an axis of the handle coupler 32 and post 34 (vertically in FIG. 15A). As seen best in FIG. 15A, the handle coupler 32 intersects the minor axis plane of the template 26 at an angle α from perpendicular, preferably between about 20-30°. In the context of a mitral repair, this angle greatly facilitates positioning of the annuloplasty ring 22 in the proper orientation relative to the annulus. The proximal ledge 92 is part of the peripheral edge 28 and forms an extension of the proximal face 50, thus changing the relative angle of the channel 36. For example, on the posterior segment 46 of the template 26 the proximal ledge 92 forms an acute angle with the distal wall 90, while on the anterior segment 44 the channel 36 defines an obtuse angle.

On the sides, as seen in FIG. 15C, the proximal angled channel 36 again defines an included acute angle. FIG. 15C illustrates a major outer dimension $D_1$ of the template 26 defined by the ledge 92 and a corresponding major dimension $d_1$ of the wall 90. As seen in FIG. 9A, the annuloplasty ring 22 conforms closely within the channel 36, against the wall 90 and underneath the ledge 92. The wall 90 thus follows the radial size of the ring 22 and therefore the major dimension $d_1$ corresponds to the inner dimension 52 of the exemplary annuloplasty ring 22 as shown in FIG. 11B along its major axis.

The minor dimension $D_2$ of the template 26 is indicated in FIG. 15A. Both the the handle coupler 32 and single cutting well 48 are desirably located along the minor axis of the holder 24, as seen in section in FIG. 15A and from above in FIG. 14B. The handle coupler 32 and cutting well 48 are advantageously spaced far apart along the minor dimension $D_2$, and desirably closely adjacent the respective anterior and posterior segments 44, 46, respectively. As mentioned, this configuration maximizes space for a surgeon to manipulate a cutting instrument within the surgical field. Moreover, the surgeon need only make one cut of the connecting filament at the single cutting well 48. The result is a highly visible and an extremely convenient means for detaching the holder 24 from the ring 22, thus eliminating guesswork and the risks attendant with having to make multiple cutting steps. In a preferred embodiment, the nearest structure of the handle coupler 32 is located between about 10-20% of the minor dimension $D_2$ from the anterior segment 44, and the nearest structure of the cutting well 48 is located between about 5-10% from the posterior segment 46. Since different ring sizes require different sized holders, the absolute values of these locations vary, as detailed below.

The following table lists the minor axis dimension $D_2$ as seen in FIG. 15A for a number of usual ring sizes, and then the distance and percentage of $D_2$ between the handle coupler 32 and the edge of the template 26. Specifically, the distance between the handle coupler 32 and the anterior segment 44 is shown as $x_1$ in FIG. 14A.

| Ring size (mm) | $D_2$ (mm) | $x_1$ (mm) | $x_1$ (% of $D_2$) |
|---|---|---|---|
| 24 | 17.526 | 2.667 | 15.2 |
| 26 | 18.466 | 3.175 | 17.2 |
| 28 | 19.533 | 3.302 | 16.9 |
| 30 | 20.853 | 3.175 | 15.2 |
| 32 | 22.200 | 2.749 | 12.4 |
| 34 | 23.647 | 3.175 | 13.4 |
| 36 | 25.451 | 3.810 | 15.0 |
| 38 | 26.975 | 5.080 | 16.9 |
| 40 | 28.423 | 5.080 | 17.9 |

The distance between the cutting well 48 and the posterior segment 46 is shown as $x_2$ in FIG. 15B. The cutting well 48 desirably has its closest wall spaced a distance $x_2$ within 1-2 mm from the peripheral edge; in a particular embodiment 1.27 mm. Preferably this distance $x_2$ does not change over the ring sizes, and the cutting well 48 remains a consistent distance form the edge of the template 26. As seen in FIG. 15B, the bridge 96 across which the connecting suture is suspended is somewhat farther from the edge, specifically between about 2-3 mm farther. In a simple example, the cutting well 48 has a slot length of about 5 mm (preferably 4.6 mm) which commences about 1 mm from the edge of the template 26, so that the bridge 96 suspends the connecting suture a distance of 3.5 mm from the template edge. This closely adjacent spacing of the cutting point from the template edge greatly facilitates the surgeon's task and substantially eliminates interference from the handle coupler 32 or attached components. Preferably, the cutting point (plane of bridge 96) is spaced from the edge of the template 26 by about 10-20% of the minor dimension $D_2$ from the posterior segment 46 of the template 26, and more preferably about 15%.

With reference back to FIG. 9B, relevant dimensions are illustrated that show the extent to which the annuloplasty ring 22 is exposed radially outward from the channel 36 (or ledge 92). The ring 22 has a radial dimension r that is larger than the radial dimension of the channel 36, and preferably ranges from 2.515 mm to 3.251 mm. As explained, and as seen in FIG. 12B, the ring 22 comprises the inner core 60 surrounded by the outer cover 62 which includes the outwardly extending sewing margin 64. The sewing margin 64 extends outward from the peripheral edge 28 (ledge 92) by a distance S that ranges from 1.245 to 1.575 mm. This results in an overhang O of the ledge 92 past the inner core 60. This overhang O helps prevent the surgeon from passing a suture needle to the inside of the core 60, or catching one of the bands 70 in a multiple band core. Desirably, the overhang O is between about 0.1178-0.3302 mm.

FIG. 15A also shows in elevation a wall 94 that forms one half of the cutting well 48. As seen from above in FIGS. 14A and 14B, the walls 94 are located adjacent the peripheral edge 28 and extend upward from the proximal face 50. Each wall 94 includes a relatively straight section parallel to the other wall, and opposite ends that curve inward toward the other wall, much like parentheses. The inwardly curved ends narrow the gap between the two walls 94 to help guide a cutting implement such as a scalpel into a midplane between the two walls. FIG. 15A shows a notch 96 on upper edge of the wall 94. The combination of the notches 96 across the two walls 94 provides a convenient bridge across which connecting filaments are suspended, as will be described in detail below with respect to FIGS. 16 and 17. The walls 94 present one configuration of cutting well that may be utilized, and of course others are contemplated. Cutting wells desirably project upward from the proximal face 50 of the template 26 so that a connecting filament can be suspended over a space within which a cutting implement can be inserted. Alternatively, a cutting well that is recessed below the proximal face may also be used, although the visibility and accessibility are somewhat reduced.

FIG. 14B indicates a gap G between the closest part of the handle coupler 32 and a line across the two notches 96 in the walls 94. This represents the spacing between the upstanding coupler 32 (or equivalent interfering structure in various ring holders) and the point at which a surgeon cuts the ring free. The gap G is larger than in previous ring holders, and desirably about half of the entire minor dimension of the holder template 26, which in turn is slightly larger than the minor dimension 52 of the ring 22 (see FIG. 11B). In a preferred embodiment, the gap G is about half of the minor dimension 52 of the ring 22, which depends on the ring size, and which corresponds to the minor radial dimension of the angled channel 36 (or wall 90). For instance, an exemplary holder 24 has angled channel 36 major and minor dimensions and gaps G as in the following table:

| Ring size (mm) | Angled channel 36 minor dimension (mm) | Angled channel 36 major dimension (mm) | Spacing between holder and cutting well, Gap G (mm) |
| --- | --- | --- | --- |
| 24 | 13.3 | 22 | 6.6 |
| 26 | 13.9 | 24 | 7.0 |
| 28 | 14.9 | 26 | 7.4 |
| 30 | 16.3 | 28 | 8.1 |
| 32 | 17.7 | 30 | 8.6 |
| 34 | 19.1 | 32 | 9.5 |
| 36 | 20.8 | 34 | 10.4 |
| 38 | 22.4 | 36 | 11.2 |
| 40 | 24.2 | 38 | 12.1 |

With particular reference to FIGS. 14B and 14C, the holder 24 includes a series of through holes for passage of a connecting filament for firmly holding an annuloplasty ring string 22 in the angled channel 36. It should be understood that although through holes are the preferred construction, other configurations that provide passages through the holder 24 and/or perform similar functions are contemplated. For example, the template 26 is provided with a pair of cleats 100a, 100b adjacent the peripheral edge 28 and on the anterior segment 44. In the illustrated embodiment, each cleat 100 comprises a pair of closely-spaced holes that pass entirely through the proximal ledge 92, such that the angled channel 36 communicates with the space above the proximal face 50. A short bridge portion recessed from the proximal face 50 connects two holes. A flexible connecting filament may be looped through the two holes and tied to itself so as to anchor the filament to the cleat 100. As will be apparent to one of skill in the art, forming or machining a pair of through holes through the proximal ledge 92 is relatively economical, and in addition the process of assembling the annuloplasty ring 22 to the holder 24 using these through holes is relatively simple. However a cleat 100 that has only a single through hole or does not utilize through holes at all is entirely within the scope of the present invention. For instance, a free end of the filament may be secured to a small projection or hook provided on the template 26, rather than looping the end through the two through holes.

The cleats 100a, 100b are spaced apart around the peripheral edge 28, preferably equidistantly from the cutting well 48. As the cutting well 48 is located adjacent the peripheral edge 28 on the posterior segment 46, the cleats 100a, 100b, being located on the anterior segment 44, are circumferentially spaced by at least 90° around the template 26 from the cutting well 48. As will be explained below, a primary flexible connecting filament has free ends anchored to the cleats 100a, 100b and a midportion that passes around the posterior segment 46 of the template 26 and over the cutting well 48.

The template 26 also includes a pair of filament loops 102a, 102b, each spaced between a corresponding cleat 100 and the cutting well 48. Again, each loop 102 comprises a pair of closely-spaced holes that pass entirely through the proximal ledge 92, such that the angled channel 36 communicates with the space above the proximal face 50. As with the cleats 100, a short bridge portion recessed from the proximal face 50 connects the two holes. A flexible connecting filament may be looped through the two holes to pass from within channel 36 over the recessed bridge and back into the channel. Again, the function of each loop 102 will be more clear below, and alternative configurations such as passages that do not pass completely through the proximal ledge 92 are contemplated.

Finally, the template 26 also includes a pair of cutting well apertures 104, 106 spaced on either side of the cutting well 48. As with the cleats 100 and loops 102, the apertures 104, 106 desirably pass entirely through the proximal ledge 92, such that the angled channel 36 communicates with the space above the proximal face 50.

FIG. 16 illustrates the exemplary annuloplasty ring holder 24 by itself and an initial step in attaching an annuloplasty ring 22 to the holder in a first procedure utilizing two connecting filaments. A first flexible connecting filament 110 anchors to one of the first cleats 100a (in the illustration, the cleat 100 on the left), so as to leave a substantially longer tail 112 and a shorter tail 114. The longer tail 112 will be used to secure the annuloplasty ring to the holder, while shorter tail 114 will be trimmed close to the cleat 100a. For security, a double square knot is desirably tied in the filament 110 on the proximal side of the cleat 100a, and the recessed bridge is sized so that the knot resides below the surface of the proximal face 50.

A second flexible connecting filament 120 anchors to one of the cutting well apertures 106 (illustration, the aperture on the right). More specifically, the filament 120 passes through the aperture 106 and around the proximal ledge 92. A square knot is tied leaving a longer tail 122 and a shorter tail 124. The longer tail 122 will be used to secure a proximal segment of the annuloplasty ring 22 to the holder 24, while the shorter tail 124 will be trimmed close to the square knot.

In FIGS. 17A-17D, the first and second flexible connecting filaments 110, 120 secure an annuloplasty ring 22 around the holder 24. A series of steps are numbered to illustrate individual movements of the filaments 110, 120 as they pass through various apertures in the holder 24 and the annuloplasty ring 22.

In the first stage shown in FIG. 17A, the assembler centers an annuloplasty ring 22 around the peripheral edge 28 of the holder 24, and in particular below the ledge 92 in the angled channel 36 (see FIG. 9A). A needle (not shown) on the free end of the longer tail 112 of the connecting filament 110 is threaded downward through one of the holes of the cleat 100a, as seen in step #1, preferably through the hole that is closest to the adjacent loop 102. After passing through the hole, the assembler loops the needle through the suture-permeable cover 62 of the ring 22, preferably through 1-2 ribs of fabric, as indicated by step #2. As mentioned above, the cover 62 desirably consists of a silicone tube covered with fabric, whereby the needle desirably passes through several strands or ribs of the fabric. From below the ring 22, the needle then passes upward in step #3 through the closest aperture in the loop 102a, and again catches 1-2 ribs of the suture-permeable cover 62 on the annuloplasty ring 22.

At this point, the first filament 110 has looped downward and upward through a portion of the annuloplasty ring, indicated by steps 1-3. Now, the assembler once again passes the first filament 110 downward through one of the holes of the loop 102a as shown in step #4. Rather than catching the needle on the annuloplasty ring 22 again, the needle and trailing filament 110 are guided around the peripheral edge 28, as seen in dashed line and indicated by step #5. In particular, the filament 110 extends along the angled channel 36 inside of the annuloplasty ring 22.

Subsequently, the assembler runs the filament 110 up through the left cutting well aperture 104, as indicated by step #6. The filament 110 loops over the cutting well 48 in step #7, and in particular over the two notches 96 (see FIG. 15B). The filament 110 then runs downward through the right cutting well aperture 106, as indicated by step #8. The assembler does not pass the filament 110 through the annuloplasty ring 22 at this point, instead running the filament around the angled channel 36, as seen in dashed line and indicated by step #9.

The next series of steps are similar to steps #1-4, but in the reverse on the other side. The filament 110 emerges from one of the holes of the right side loop 102b in step #10, and passes downward through the other hole of the loop in step #11. At this point, the assembler loops the needle through 1-2 ribs of the suture-permeable cover 62 of the ring 22, as indicated by step #12. The filament emerges through one of the holes of the right side cleat 100b, and is then passed the downward through the other hole of the cleat. To complete the process of anchoring the first filament 110 it is looped back upward through the first hole of the cleat 100b and pulled snug. Two double knots are then tied between the two holes of the right side cleat 100b, which resides in the recessed bridge area. Any remaining free end of the filament 110 can be severed close to the knots or threaded back downward through one of the holes of the cleat 100b.

At this point, the assembly is shown in FIG. 17B with only the first filament 110 securing the ring 22 to the holder 24. The filament 110 loops through the ring 22 in two places, on the anterior side between the respective cleats 100 and loops 102 (steps #2 and #12). The first filament 110 does not pass through the ring 22 around the posterior side so that it can be severed at the cutting well 48 and easily pulled free from the ring when the holder 24 is removed. Of course, additional points of anchoring the ring around the circumference of the holder 24 may be deemed necessary.

FIG. 17C shows the first several steps in anchoring the second filament 120. The longer tail 122 (FIG. 16) runs over the cutting well 48 in step #1, and downward into the left cutting well aperture 104 in step 2. The assembler then passes the needle and second filament 120 through several strands or ribs of the fabric of the ring cover 60, represented by step #3. The second filament 120 then emerges above the template 26 through the right cutting well aperture 106, as seen in step #4. The filament 120 may be passed through the ring cover 60 twice in this sequence, first as it passes downward through aperture 104, and a second time as it passes upward through aperture 106. The longer tail 122 is then secured to the shorter tail and 24 using a not such as a double square knot. The free ends are trimmed and tucked between the ring 22 and holder 24.

The final assembly is seen in FIG. 17D. The two filaments 110, 120 are both anchored to the holder 24 and have a midportion extending over the cutting well 48. A single cutting motion by the surgeon at the cutting well 48 servers the filaments 110, 120, and allows the holder 24 to be pulled straight upward from the ring 22. This step of course is done after tying off the implant sutures to secure the ring 22 against the annulus. Because the longer filament 110 does not pass through posterior side of the ring 22, the surgeon experiences relatively little frictional resistance as he/she pulls the holder 24 upward and the filaments pull free from the outer cover 60 of the ring.

FIG. 18 illustrates the exemplary annuloplasty ring holder 24 by itself and an initial step in attaching an annuloplasty ring 22 to the holder in a second procedure utilizing a single connecting filament. The procedure is very similar to the two filament process described above, and like elements will be given the same numbers. A flexible connecting filament 110 anchors to one of the first cleats 100a so as to leave a substantially longer tail 112 and a shorter tail 114. A double square knot is desirably tied in the filament 110 on the proximal side of the cleat 100a, and recessed below the surface of the proximal face 50.

FIG. 19A shows how the flexible connecting filament 110 secures an annuloplasty ring 22 around the holder 24. The assembler centers an annuloplasty ring 22 around the peripheral edge 28 of the holder 24, and in particular below the ledge 92 in the angled channel 36 (FIG. 9A). A needle on the free end of the longer tail 112 of the connecting filament 110 is threaded downward through one of the holes of the cleat 100a, as seen in step #1, preferably through the hole that is closest to the adjacent loop 102. After passing through the hole, the assembler loops the needle through the suture-permeable cover 62 of the ring 22, as indicated by step #2. From below the ring 22, the needle then passes upward in step #3 through the closest aperture in the loop 102a, and again catches a portion of the suture-permeable cover 62 on the annuloplasty ring 22.

At this point, the filament 110 has looped downward and upward through a portion of the annuloplasty ring, indicated by steps 1-3. Now, the assembler once again passes the filament 110 downward through one of the holes of the loop 102a as shown in step #4. Rather than catching the needle on the annuloplasty ring 22 again, the needle and trailing filament 110 are guided around the peripheral edge 28, as seen in dashed line and indicated by step #5. In particular, the filament 110 extends along the angled channel 36 inside of the annuloplasty ring 22.

Subsequently, the assembler runs the filament 110 up through the left cutting well aperture 104, as indicated by step #6, but this time catches a portion of the suture-permeable cover 62. The filament 110 loops over the cutting well 48 in step #7, and in particular over the two notches 96 (see FIG. 15B). The filament 110 then runs downward through the right cutting well aperture 106, as indicated by step #8, and again catches a portion of the suture-permeable cover 62. Passing the filament 110 through the ring cover 62 on the posterior side like this obviates the need for the second filament 120 described above. The ring 22 remains firmly held against the template channel with only a single connecting filament 110. The assembler then extends the filament around the angled channel 36, as seen in dashed line and indicated by step #9.

The next series of steps are similar to steps #1-4, but in the reverse on the other side. The filament 110 emerges from one of the holes of the right side loop 102b in step #10, and passes downward through the other hole of the loop in step #11. At this point, the assembler loops the needle through the suture-permeable cover 62 of the ring 22, as indicated by step #12. The filament emerges through one of the holes of the right side cleat 100b, and is then passed the downward through the other hole of the cleat. To complete the process of anchoring the filament 110 it is looped back upward through the first hole of the cleat 100*b* and pulled snug. Two double knots are then tied between the two holes of the right side cleat 100*b*, which resides in the recessed bridge area. Any remaining free end of the filament 110 can be severed close to the knots or threaded back downward through one of the holes of the cleat 100*b*.

At this point, the assembly is shown in FIGS. 19B and 19C with the single filament 110 securing the ring 22 to the holder 24. The filament 110 loops through the ring 22 in four places—on the anterior side between the respective cleats 100 and loops 102 (steps #2 and #12), and on the posterior side between on both sides of the cutting well 38 (steps #6 and #8). Of course, additional points of anchoring the ring around the circumference of the holder 24 may be deemed necessary. A seen from the anterior side in FIG. 19C, another double knot is tied in the filament 110 between the cleats 100*a*, 100*b* (see FIG. 16). A double square knot 128 is used, and then both tails are trimmed to about 5 mm in length and tucked under the holder ledge 92.

FIG. 20 is an elevational view of a modified holder 20' of the present invention attached to a prosthetic heart valve 130. The particular prosthetic heart from 130 shown is a flexible leaflet valve having a sewing ring 132 around its inflow end. The modified holder 20' attaches to the sewing ring 132 in the same manner as the earlier-described holder 20 attaches to an annuloplasty ring. That is, filaments anchored to the modified holder 20' pass through the sewing ring 132. The holder 20' is modified in this embodiment by providing a relatively planar template that conforms to the planar sewing ring 132. This illustration also shows how a holder of the present invention can be modified for planar annuloplasty rings. Furthermore, some heart valves have sewing ring that follow three-dimensional paths, and the holder of the present invention can also be modified to conform to such non-planar structures.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An annuloplasty ring and holder assembly, comprising:
   an annuloplasty ring including a suture-permeable outer cover;
   a template having an upper, proximal face and a lower, distal face and a peripheral edge sized and adapted to receive the annuloplasty ring in conformal contact therewith, the upper, proximal face of the template having a single cutting well adjacent the peripheral edge defined by a pair of spaced apart walls extending upward from the proximal face, and two spaced cleats adjacent the template peripheral edge each positioned at least 90° circumferentially around the peripheral edge from the single cutting well; and
   a flexible connecting filament having its free ends anchored to the two spaced cleats and a mid-portion passing through at least two points on the annuloplasty ring outer cover and emerging above the proximal face of the template at only one location where it is suspended across the single cutting well.

2. The assembly of claim 1, wherein the two spaced cleats are equidistantly positioned circumferentially around the peripheral edge from the cutting well.

3. The assembly of claim 1, wherein the template peripheral edge defines a substantially angled channel for receiving the annuloplasty ring formed by a distal wall and an outwardly extending proximal ledge defining an outer extent of the template.

4. The assembly of claim 3, wherein the included angle of the angled channel between the distal wall and the proximal ledge varies around the peripheral edge.

5. The assembly of claim 1, wherein the template peripheral edge includes an outwardly extending proximal ledge, and wherein the two spaced cleats are each formed by a first pair of holes through the proximal ledge recessed below the proximal face.

6. The assembly of claim 5, further including a second pair of holes through the proximal ledge located between each of the first pairs of holes and the cutting well, wherein the filament ties to each first pair of holes, passes through the annuloplasty ring outer cover, loops up and down through the second pair of holes, and continues under the proximal ledge until emerging above the proximal face of the template to be suspended across the cutting well.

7. The assembly of claim 1, wherein the template further includes a coupler to which a handle member connects, the coupler being located adjacent the peripheral edge diametrically opposite the cutting well.

8. The assembly of claim 1, wherein the annuloplasty ring includes a generally rigid inner core surrounded by the suture-permeable outer cover, the template peripheral edge is partly formed by an outwardly extending proximal ledge defining an outer extent of the template, and wherein the proximal ledge extends radially outward from the rigid inner core when the annuloplasty ring is received in conformal contact with the peripheral edge and the suture-permeable outer cover extends outward from the proximal ledge.

9. The assembly of claim 1, further including a second flexible connecting filament anchored to the template at two free ends near to the cutting well, wherein a portion of the second flexible connecting filament extends above the proximal face of the template where it is suspended across the cutting well.

10. An annuloplasty ring holder, comprising:
    a template having an upper, proximal face and a lower, distal face and a peripheral edge sized and adapted to receive an annuloplasty ring in conformal contact therewith, the upper, proximal face of the template having a single flexible connecting filament cutting well adjacent the peripheral edge defined by a pair of spaced apart walls extending upward from the proximal face, wherein the template further includes a coupler to which a handle member connects, the coupler being offset from a center of the proximal face of the template and located closer to the peripheral edge diametrically opposite the cutting well than to the cutting well.

11. The holder of claim 10, wherein the template peripheral edge has a major axis and major dimension and a minor axis and minor dimension smaller than the major dimension, and the single cutting well is located along the minor axis.

12. The holder of claim 10, wherein the template peripheral edge circumscribes at least one visibility window that occupies a majority of the cross-sectional area within the peripheral edge.

13. The holder of claim 10, wherein the template peripheral edge defines a substantially angled channel for receiving the annuloplasty ring formed by a distal wall and an outwardly extending proximal ledge defining an outer extent of the template.

14. The holder of claim 13, wherein the included angle of the angled channel between the distal wall and the proximal ledge varies around the peripheral edge.

15. The holder of claim 10, wherein the template includes two spaced cleats adjacent the template peripheral edge each positioned at least 90° circumferentially around the peripheral edge from the cutting well and to which a flexible connecting filament may be anchored.

16. The holder of claim 10, wherein the template peripheral edge is generally arranged around a central axis and defines a channel for receiving the annuloplasty ring formed by a distal wall and a radially outwardly extending proximal ledge, and the coupler extends in a proximal direction that is generally parallel to the direction the distal wall extends but is not parallel to the central axis.

17. The holder of claim 10, wherein the template peripheral edge is generally arranged around a central axis and the coupler and cutting well are diametrically opposed to each other along a line through the central axis which has a dimension $D_2$, and wherein the closest portion of the coupler is located between about 10-20% of the dimension $D_2$ from the nearest peripheral edge and the closest portion of the cutting well is located between about 5-10% of the dimension $D_2$ from the nearest peripheral edge.

18. The holder of claim 10, wherein the template peripheral edge is generally arranged around a central axis and the coupler and cutting well are diametrically opposed to each other along a line through the central axis which has a dimension $D_2$, and wherein the closest portion of the coupler is located between about 3-5 mm from the nearest peripheral edge and the closest portion of the cutting well is located between about 1-2 mm from the nearest peripheral edge.

19. The holder of claim 10, wherein the template further includes two spaced cleats adjacent the template peripheral edge each positioned at least 90° circumferentially around the peripheral edge from the cutting well.

20. The holder of claim 10, wherein the template is sized and shaped for holding a mitral annuloplasty ring, and includes a major axis and major dimension and a minor axis and minor dimension smaller than the major dimension, and the single cutting well is located along the minor axis, and wherein the minor axis extends from an anterior segment to a posterior segment of the peripheral edge, with the anterior segment being straighter than the posterior segment, and wherein the coupler is located adjacent the anterior segment and the cutting well is located adjacent the posterior segment.

21. The holder of claim 20, wherein the template has a saddle shape with the peripheral edges on both sides of the peripheral edge along the major axis curving in a distal direction from a central portion of the template.

* * * * *